US008980551B2

(12) United States Patent
Warthmann et al.

(10) Patent No.: US 8,980,551 B2
(45) Date of Patent: Mar. 17, 2015

(54) USE OF CLASS IIB RESTRICTION ENDONUCLEASES IN 2$^{nd}$ GENERATION SEQUENCING APPLICATIONS

(75) Inventors: Norman Warthmann, Bad Reichenhall (DE); Detlef Weigel, Tübingen (DE)

(73) Assignee: Max-Planck-Gesellschaft Zur Forderung der Wissenschaften E.V., Munich (DE)

( * ) Notice: Subject to any disclaimer, the term of this patent is extended or adjusted under 35 U.S.C. 154(b) by 389 days.

(21) Appl. No.: 13/318,278

(22) PCT Filed: May 5, 2010

(86) PCT No.: PCT/EP2010/056132
§ 371 (c)(1),
(2), (4) Date: Dec. 15, 2011

(87) PCT Pub. No.: WO2010/128091
PCT Pub. Date: Nov. 11, 2010

(65) Prior Publication Data
US 2012/0094847 A1    Apr. 19, 2012

(30) Foreign Application Priority Data
May 5, 2009   (EP) .................................. 09006133

(51) Int. Cl.
C12Q 1/68 (2006.01)
C12P 19/34 (2006.01)
C07H 21/00 (2006.01)
C07H 21/02 (2006.01)
C07H 21/04 (2006.01)
C12N 15/64 (2006.01)
C12N 15/10 (2006.01)
C12N 15/66 (2006.01)

(52) U.S. Cl.
CPC ............ C12N 15/64 (2013.01); C12N 15/1065 (2013.01); C12N 15/66 (2013.01)
USPC .......... 435/6.1; 435/91.2; 536/22.1; 536/23.1; 536/24.3

(58) Field of Classification Search
CPC .... C12N 15/1065; C12N 15/64; C12N 15/66; C12Q 1/6806; C12Q 2521/313; C12Q 2539/103; C12Q 1/44; C12Q 1/6874; C12Q 1/6858; C12Q 2521/331; C12Q 2563/149; C12Q 1/6816; C12Q 1/6809; C12Q 1/683; C12Q 2521/301; C12Q 1/6869; C12Q 2521/501; C12Q 2525/131; C12Q 1/6855; C12Q 1/6844; C12Q 2525/191; C12Q 2521/307; C12Q 2525/101; C12Q 1/6853; C12Q 1/686; C12Q 2521/525; C12Q 2537/143; C12Q 2531/113; C12Q 2525/301; C12Q 2545/101; C12Q 2537/165; C12Q 2537/16; C12Q 2535/122; C12Q 1/6883
USPC .................. 435/6.1; 536/22.1, 23.1, 24.3
See application file for complete search history.

(56) References Cited

U.S. PATENT DOCUMENTS

| | | | |
|---|---|---|---|
| 6,372,434 B1 * | 4/2002 | Weissman et al. ........... | 435/6.13 |
| 6,534,293 B1 | 3/2003 | Barany et al. | |
| 6,977,162 B2 * | 12/2005 | Dhallan ...................... | 435/91.2 |
| 8,178,300 B2 * | 5/2012 | Van Eijk et al. ............. | 435/6.12 |
| 2003/0186251 A1 | 10/2003 | Dunn et al. | |
| 2006/0292597 A1 | 12/2006 | Shapero et al. | |
| 2010/0304990 A1 * | 12/2010 | Gifford et al. ................. | 506/9 |

FOREIGN PATENT DOCUMENTS

| | | | |
|---|---|---|---|
| WO | 93/06239 A1 | 4/1993 | |
| WO | 98/51789 A2 | 11/1998 | |
| WO | 00/24939 A1 | 5/2000 | |
| WO | 03/022986 A2 | 3/2003 | |
| WO | 2004/033721 A2 | 4/2004 | |
| WO | 2005/079357 A2 | 9/2005 | |
| WO | 2006/137734 A1 | 12/2006 | |
| WO | WO 2007/114693 | * | 10/2007 |
| WO | 2008/007951 A1 | 1/2008 | |
| WO | WO 2008/045575 | * | 4/2008 |

OTHER PUBLICATIONS

Tengs et al. Genomic representations using concatenates of Type IIB restriction endonuclease digestion fragments. Nucleic Acids Research 32 (15) : e121 (2004).*
Wang et al., Digital karyotyping. PNAS 99 (25) : 16156 (2002).*
International Search Report issued in International Application No. PCT/EP2010/056132, (Oct. 31, 2011).

* cited by examiner

*Primary Examiner* — Ethan C Whisenant
(74) *Attorney, Agent, or Firm* — Morgan, Lewis & Bockius, LLP

(57) ABSTRACT

The present invention relates to a method for genotyping DNA molecules contained in at least one DNA sample. The method includes: (a) digesting the DNA molecules contained in at least one DNA sample with a class IIB restriction endonuclease to generate DNA fragments; (b) optionally separating DNA fragments comprising the recognition site for the class IIB restriction endonuclease from the remaining DNA fragments; (c) attaching at least one adaptor DNA to the 5' and/or 3' end of one or both strands of the DNA fragments comprising the recognition site for the class IIB restriction endonuclease obtained in a) or separated in b) to form adaptor-fragment constructs; (d) determining the sequence of at least a fraction of the DNA fragments obtained in c); and (e) assigning genotypes to the at least one DNA sample analyzed based on the sequence data obtained in d). The present invention further relates to method for determining the position of DNA molecules comprised in a DNA library within the DNA sequence represented by the DNA library or within a known DNA sequence and for establishing a cross-reference between individual DNA molecules and their location in an at least three dimensional matrix.

9 Claims, 11 Drawing Sheets

Figure 1:
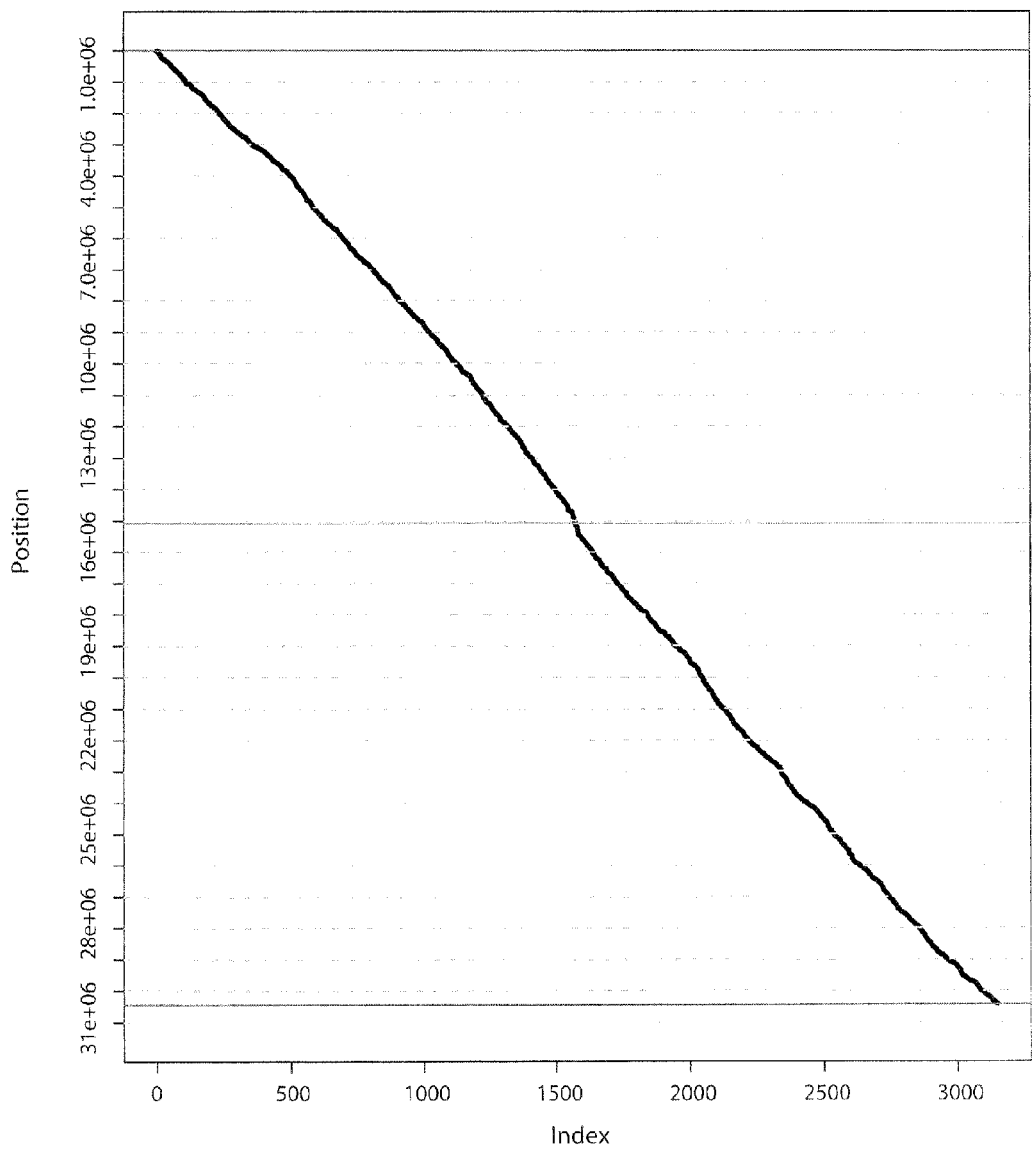

SEQUENCE LISTING

<160> NUMBER OF SEQ ID NOS: 18

<210> SEQ ID NO 1
<211> LENGTH: 21
<212> TYPE: DNA
<213> ORGANISM: Artificial sequence
<220> FEATURE:
<223> OTHER INFORMATION: /note="Description of artificial sequence:
      example of DNA adaptor"

<400> SEQUENCE: 1
agatcggaag agcacacgtc t                                           21

<210> SEQ ID NO 2
<211> LENGTH: 35
<212> TYPE: DNA
<213> ORGANISM: Artificial sequence
<220> FEATURE:
<223> OTHER INFORMATION: /note="Description of artificial sequence:
      example of DNA adaptor"

<400> SEQUENCE: 2
acactctttc cctacacgac gctcttccga tctaa                            35

<210> SEQ ID NO 3
<211> LENGTH: 65
<212> TYPE: DNA
<213> ORGANISM: Artificial sequence
<220> FEATURE:
<223> OTHER INFORMATION: /note="Description of artificial sequence:
      method of Figure 3: example of a single-stranded 36 bp fragment
      after restriction digest with Type IIB enzyme coupled to a homopolymeric polynucleotide"

<400> SEQUENCE: 3
cccccccccc cccccccccc cccccccccc ccccccttttt tttttttttt tttttttttt    60
ttttc                                                                  65

<210> SEQ ID NO 4
<211> LENGTH: 43
<212> TYPE: DNA
<213> ORGANISM: Artificial sequence
<220> FEATURE:
<223> OTHER INFORMATION: /note="Description of artificial sequence:
      method of Figure 3: example of a single-stranded oligonucleotide
      primer comprising homopolymeric 3'-end"

<400> SEQUENCE: 4
cccccccccc cccccccccc ccaaaaaaaa aaaaaaaaaa aac                        43

<210> SEQ ID NO 5
<211> LENGTH: 76
<212> TYPE: DNA
<213> ORGANISM: Artificial sequence
<220> FEATURE:
<223> OTHER INFORMATION: /note="Description of artificial sequence:
      method of Figure 3: example of DNA fragment after action of Klenow
      fragment"

<400> SEQUENCE: 5
cccccccccc cccccccccc cccccccccc ccccttttt tttttttttt ttttcccccc       60
cccccccccc cccccc                                                      76

<210> SEQ ID NO 6
<211> LENGTH: 77
<212> TYPE: DNA
<213> ORGANISM: Artificial sequence
<220> FEATURE:
<223> OTHER INFORMATION: /note="Description of artificial sequence:
      method of Figure 3: example of DNA fragment after action of Klenow
      fragment"

<400> SEQUENCE: 6
cccccccccc cccccccccc ccaaaaaaaa aaaaaaaaaa aaccccccccc cccccccccc     60 cccccccccc ccccccc                                                     77

<210> SEQ ID NO 7
<211> LENGTH: 109
<212> TYPE: DNA
<213> ORGANISM: Artificial sequence
<220> FEATURE:
<223> OTHER INFORMATION: /note="Description of artificial sequence:
      method of Figure 3: example of DNA fragment after action of Klenow
      (exo-) and dATPs and ligation of adaptor"

<400> SEQUENCE: 7
cccccccccc cccccccccc cccccccccc cctcccccc cccccccccc cccccccccc      60 ccccccttt tttttttttt ttttttttccc cccccccccc ccccccccc                  109

<210> SEQ ID NO 8
<211> LENGTH: 109
<212> TYPE: DNA
<213> ORGANISM: Artificial sequence
<220> FEATURE:
<223> OTHER INFORMATION: /note="Description of artificial sequence:
      method of Figure 3: example of DNA fragment after action of Klenow
      (exo-) and dATPs and ligation of adaptor"

<400> SEQUENCE: 8
cccccccccc cccccccccc ccaaaaaaaa aaaaaaaaaa aacccccccc cccccccccc    60
cccccccccc ccccccaccc cccccccccc cccccccccc ccccccccc               109

<210> SEQ ID NO 9
<211> LENGTH: 131
<212> TYPE: DNA
<213> ORGANISM: Artificial sequence
<220> FEATURE:
<223> OTHER INFORMATION: /note="Description of artificial sequence:
      method of Figure 3: example of a DNA fragment of SEQ ID NO: 7
      after amplification"

<400> SEQUENCE: 9
cccccccccc cccccccccc cccccccccc cccccccccc cccccccccc ccctccccc    60 cccccccccc cccccccccc cccccccct tttttttttt tttttttttc cccccccccc    120
cccccccccc c                                                         131

<210> SEQ ID NO 10
<211> LENGTH: 132
<212> TYPE: DNA
<213> ORGANISM: Artificial sequence
<220> FEATURE:
<223> OTHER INFORMATION: /note="Description of artificial sequence:
      method of Figure 3: specific example of DNA fragment of SEQ ID NO:
      7 after amplification"

<400> SEQUENCE: 10
aatgatacgg cgaccaccga caggttcaga gttctacagt ccgacgatca aaaataaaaa    60
aaaaaaaaaa aaaaaaaaaa aaaaaaaaaa attttttttt tttttttttt cgtatgccgt    120
cttctgcttg tt                                                        132

<210> SEQ ID NO 11
<211> LENGTH: 79
<212> TYPE: DNA
<213> ORGANISM: Artificial sequence
<220> FEATURE:
<223> OTHER INFORMATION: /note="Description of artificial sequence:
      nucleotide sequence contained in Phage Lambda"

<400> SEQUENCE: 11
aagctcaaca cgcagtttcc ctactgttag cgcaatatcc tcgttctcct ggtcgcggcg    60
tttgatgtat tgctggttc                                                 79

<210> SEQ ID NO 12
<211> LENGTH: 50
<212> TYPE: DNA
<213> ORGANISM: Artificial sequence
<220> FEATURE:
<223> OTHER INFORMATION: /note="Description of artificial sequence:
      example of sequenced barcoded tags stemming from processing DNA
      from the Phage Lambda through the procedure of the present
      invention"

<400> SEQUENCE: 12
aaaaaaagaa cctactgtta gcgcaatatc ctcgttctcc tggtatggtt              50

<210> SEQ ID NO 13
<211> LENGTH: 49
<212> TYPE: DNA
<213> ORGANISM: Artificial sequence
<220> FEATURE:

```
<223> OTHER INFORMATION: /note="Description of artificial sequence:
      example of sequenced barcoded tags stemming from processing DNA
      from the Phage Lambda through the procedure of the present
      invention"

<400> SEQUENCE: 13
aaaaaaaaac ctactgttag cgcaatatcc tcgttctcct ggtatggtt          49

<210> SEQ ID NO 14
<211> LENGTH: 44
<212> TYPE: DNA
<213> ORGANISM: Artificial sequence
<220> FEATURE:
<223> OTHER INFORMATION: /note="Description of artificial sequence:
      example of sequenced barcoded tags stemming from processing DNA
      from the Phage Lambda through the procedure of the present
      invention"

<400> SEQUENCE: 14
aaccattact gttagcgcaa tatcctcgtt ctcctggtcg tttt               44

<210> SEQ ID NO 15
<211> LENGTH: 47
<212> TYPE: DNA
<213> ORGANISM: Artificial sequence
<220> FEATURE:
<223> OTHER INFORMATION: /note="Description of artificial sequence:
      example of sequenced barcoded tags stemming from processing DNA
      from the Phage Lambda through the procedure of the present
      invention"

<400> SEQUENCE: 15
aaccattact gttagcgcaa tatcctcgtt ctcctggtcg ttttttt            47

<210> SEQ ID NO 16
<211> LENGTH: 48
<212> TYPE: DNA
<213> ORGANISM: Artificial sequence
<220> FEATURE:
<223> OTHER INFORMATION: /note="Description of artificial sequence:
      example of sequenced barcoded tags stemming from processing DNA
      from the Phage Lambda through the procedure of the present
      invention"

<400> SEQUENCE: 16
aaccattact gttagcgcaa tatcctcgtt ctcctggtcg tttttttt           48

<210> SEQ ID NO 17
<211> LENGTH: 48
<212> TYPE: DNA
<213> ORGANISM: Artificial sequence
<220> FEATURE:
<223> OTHER INFORMATION: /note="Description of artificial sequence:
      example of sequenced barcoded tags stemming from processing DNA
      from the Phage Lambda through the procedure of the present
      invention"

<400> SEQUENCE: 17
aaccattact gttagcgcaa tatcctcgtt ctcctggtcg tttttttt           48

<210> SEQ ID NO 18
<211> LENGTH: 80
<212> TYPE: DNA
<213> ORGANISM: Artificial sequence
<220> FEATURE:
<223> OTHER INFORMATION: /note="Description of artificial sequence:
      consensus sequence of SEQ ID NOs. 11 to 17"

<400> SEQUENCE: 18
```

```
aagctcaaca aaaaaaatac ctactgttag cgcaatatcc tcgttctcct ggtcgaggcg      60
tttgatgtat tgctggtttc                                                  80
```

USE OF CLASS IIB RESTRICTION ENDONUCLEASES IN 2$^{nd}$ GENERATION SEQUENCING APPLICATIONS

CROSS-REFERENCE TO RELATED APPLICATIONS

The present application is a U.S. National Stage of International Application No. PCT/EP2010/056132, filed 5 May 2010, which claims priority to European Patent Application No. 09006133.4, filed 5 May 2009, the contents of which are hereby incorporated by reference in their entirety.

The present invention relates to a method for genotyping DNA molecules contained in at least one DNA sample comprising: (a) digesting the DNA molecules contained in at least one DNA sample with a class IIB restriction endonuclease to generate DNA fragments; (b) optionally separating DNA fragments comprising the recognition site for said class IIB restriction endonuclease from the remaining DNA fragments; (c) attaching at least one adaptor DNA to the 5' and/or 3' end of one or both strands of the DNA fragments comprising the recognition site for said class IIB restriction endonuclease obtained in a) or separated in b) to form adaptor-fragment constructs; (d) determining the sequence of at least a fraction of the DNA fragments obtained in c); and (e) assigning genotypes to said at least one DNA sample analysed based on the sequence data obtained in d). The present invention further relates to method for determining the position of DNA molecules comprised in a DNA library within the DNA sequence represented by said DNA library or within a known DNA sequence and for establishing a cross-reference between individual DNA molecules and their location in an at least three dimensional matrix.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The development of high-throughput sequencing techniques (2$^{nd}$ generation sequencing) greatly facilitates many applications including the retrieval of genomic information. 2nd generation sequencing is not yet used for genotyping or haplotyping. Genotyping is currently the state of the art for genome wide comparisons of the genetic mark-up of individuals of a species, be it unicellular or multicellular.

Until now, if sequencing is used and no prior information of the DNA sequence and markers is available, large amounts of data are needed in order to obtain enough comparable information across individuals. The retrieval of these data is cost intensive in terms of the materials and time.

High throughput sequencing techniques utilize randomly fragmented DNA samples which are amplified by attaching a universal sequence to each fragment. This facilitates amplification and subsequent analysis. Common techniques are practiced in emulsions or on a solid surface. Such methods are, e.g., described in WO98/44151 or WO00/18957, wherein an amplification step called bridging amplification is carried out on a solid surface prior to sequencing leading to a cluster of identical polynucleotides thus facilitating sequence detection. Similar procedures without bridging amplification are described in WO2008/093098. Further sequencing techniques are disclosed in U.S. Pat. No. 5,902,723, U.S. Pat. No. 6,403,320, U.S. Pat. No. 6,420,169, U.S. Pat. No. 6,576,424, U.S. Pat. No. 7,056,666 and U.S. Pat. No. 0,834,575.

It is possible to sequence DNA from more than one sample by barcoding each sample prior to application to the sequencing process. Fluorescent tags limit the number of samples to be analysed to the number of differently detectable tags available. On the other hand, DNA barcodes consisting of 2 or more bases depending on the number of samples to be analysed can be used to label each sample. One way of attaching barcodes to DNA samples is described in U.S. Pat. No. 5,604,097. In connection with sequencing on beads, barcodes can be used to sort thus labelled DNA samples to the respective beads coated with primers complementary to one specific sample barcode (see Brenner et al., 2000, Nature Biotechnol. June; 18(6):630-4.). A technique enabling for sequencing the barcodes attached to DNA samples is provided e.g. in WO2004/069849 or WO2006/099579.

High-throughput approaches have been developed relying on the idea of representational subsampling to screen a large number of nucleic acid loci by hybridization or sequencing. These methods are based on the possibility to analyse a large genome by detailed analysis of a representational subset of the original sequence. Serial analysis of gene expression (SAGE) (Velculescu et al., 1995, Science 270(5235), pp. 484-487) relies on analyses of concatenates of short cDNA tags for transcriptional profiling. Digital karyotyping (Wang et al., 2002, PNAS 99 (25): 16156-16161) uses a similar technique to karyotype genomes in order to identify loci that are amplified or (partially) deleted.

One method to characterize BAC libraries by sequencing relies on the partial end-sequencing of large restriction fragments. The fragments obtained after restriction of clones of a BAC library with one or several restriction endonucleases are partially sequenced from both sides to retrieve short sequence fragments which can be used for positioning said clones within the BAC library or to one another. Thereby, the data to be analyzed is already reduced, however, it still requires many different enzymes and a large sequencing effort to ensure overlapping information. It would thus be advantageous to have even more convenient methods available which reduce the sequencing effort.

Accordingly, the present invention relates to a method for genotyping DNA molecules contained in at least one DNA sample comprising: (a) digesting the DNA molecules contained in at least one DNA sample with a class IIB restriction endonuclease to generate DNA fragments; (b) optionally separating DNA fragments comprising the recognition site for said class IIB restriction endonuclease from the remaining DNA fragments; (c) attaching at least one adaptor DNA to the 5' and/or 3' end of one or both strands of the DNA fragments comprising the recognition site for said class IIB restriction endonuclease obtained in a) or separated in b) to form adaptor-fragment constructs; (d) determining the sequence of at least a fraction of the DNA fragments obtained in c); and (e) assigning genotypes to said at least one DNA sample analysed based on the sequence data obtained in d).

Unless indicated otherwise, the sequence of steps to be effected in the method of the invention is as listed in the respective embodiments.

The term "genotyping" relates to the interrogation of allele status at least one particular locus in a genome of at least one individual. A known difference in allele status (i.e. a difference in the nucleic acid sequences) between members of a population is known as a marker. Such markers are, inter alia, single-nucleotide polymorphisms (SNPs), wherein the most common ones have only two alleles. If individuals are genotyped genome-wide, then many markers along the chromosomes are independently assayed. For these assays, DNA sequence information of the locus of interest surrounding the marker is necessary. There are many different genotyping technologies well known to a person skilled in the art.

The term "polymorphism" as is used in the present invention includes not only single nucleotide substitutions, but also nucleotide insertions and nucleotide deletions of one or more nucleotides at a position of a DNA molecule, preferably as compared to a reference DNA molecule.

A polymorphism may fall within the coding sequences or the non-coding regions of genes or within the intergenic regions between the genes. Also non-coding polymorphisms can have phenotypic effects: Polymorphisms in the 5' untranslated region (5'UTR) of genes can affect the efficiency with which the protein is translated. A representative example of this is in the c-myc gene where a C-G SNP that creates an internal ribosome entry site is associated with increased efficiency of c-myc translation and myeloma (Chappell et al., Oncogene 19 (2000), 4437-4440). Polymorphisms in the 3'UTR can affect gene function by altering the secondary structure of RNA and efficiency of translation or by affecting motifs in the RNA that bind proteins which regulate RNA degradation. Polymorphisms within introns can affect gene function by affecting RNA splicing resulting in aberrant polypeptides. Another way in which intronic polymorphisms can affect gene function is when they affect regulatory motifs within introns. Examples are the Sp1 binding site polymorphism within intron 1 of the COLIA1 gene (Mann et al., J. Clin. Invest 107 (2001), 899-907) and repeat polymorphisms within the IL-1Ra gene (Keen et al., Bone 23 (1998), 367-371).

The term "DNA molecule", interchangeably used with "DNA" refers to desoxyribonucleic acid which is found in the cell nucleus and, to a lesser extent, in certain cell organelles such as mitochondria and chloroplasts to form the genetic information of the cell. In the context of the present invention, the term refers to genomic DNA as well as cDNA which is e.g. produced by reverse transcribing RNA using reverse transcriptases. A reverse transcriptase is an enzyme that catalyzes the polymerization of deoxyribonucleoside triphosphates to form primer extension products that are complementary to a ribonucleic acid template. The enzyme initiates synthesis at the 3'-end of the primer and proceeds toward the 5'-end of the template until synthesis terminates. Examples of suitable polymerizing agents that convert the RNA target sequence into a complementary, copy-DNA (cDNA) sequence are avian myeloblastosis virus reverse transcriptase and *Thermus thermophilus* DNA polymerase, a thermostable DNA polymerase with reverse transcriptase activity marketed by Perkin Elmer. Typically, the genomic RNA/cDNA duplex template is heat denatured during the first denaturation step after the initial reverse transcription step leaving the DNA strand available as an amplification template. High-temperature RT provides greater primer specificity and improved efficiency. U.S. patent application Ser. No. 07/746,121, filed Aug. 15, 1991, describes a "homogeneous RT-PCR" in which the same primers and polymerase suffice for both the reverse transcription and the PCR amplification steps, and the reaction conditions are optimized so that both reactions occur without a change of reagents. *Thermus thermophilus* DNA polymerase, a thermostable DNA polymerase that can function as a reverse transcriptase, can be used for all primer extension steps, regardless of template. Both processes can be done without having to open the tube to change or add reagents; only the temperature profile is adjusted between the first cycle (RNA template) and the rest of the amplification cycles (DNA template). The RT reaction can be performed, for example, in a 20 µl reaction mix containing: 4 µl of 5×AMV-RT buffer, 2 µl of Oligo dT (100 µg/ml), 2 µl of 10 mM dNTPs, 1 µl total RNA, 10 Units of AMV reverse transcriptase, and $H_2O$ to 20 µl final volume. The reaction may be, for example, performed by using the following conditions: The reaction is held at 70 C. ° for 15 minutes to allow for reverse transcription. The reaction temperature is then raised to 95 C. ° for 1 minute to denature the RNA-cDNA duplex. Next, the reaction temperature undergoes two cycles of 95° C. for 15 seconds and 60 C. ° for 20 seconds followed by 38 cycles of 90 C. ° for 15 seconds and 60 C. ° for 20 seconds. Finally, the reaction temperature is held at 60 C. ° for 4 minutes for the final extension step, cooled to 15 C. °, and held at that temperature until further processing of the amplified sample. Any of the above mentioned reaction conditions may be scaled up according to the needs of the particular case.

A "DNA sample" in the context of the present invention is a probe containing DNA. Samples can be directly taken from cell cultures or from an individual or from a conserved source such as a library. The DNA contained in a DNA sample may represent a part of or the entire genetic information of an organism. The DNA sample may include intron, exon and intergenic sequences but may as well be comprised of genes only (UTRs, exons, introns). Alternatively, subsets of the genetic information can be used such as one or more single chromosomes or parts thereof or organelle genomes.

The present method uses at least one DNA sample. If more than one sample is used, the origin of said samples may be the same, such as the same species, or different such as different species or subspecies. Different DNA samples may also stem from different individuals of one or more species. If the origin is the same individual then a sample can still represent a different subset of its DNA (BAC, YAC clones). A DNA sample can also be a pool of said samples.

The term "digesting" refers to the controlled decomposition of DNA, which is effected using restriction endonucleases with known recognition and/or cleavage sites. Restriction endonucleases are enzymes that cleave the sugar-phosphate backbone of DNA, usually both strands of double-stranded DNA within a stretch of just a few bases. Several thousand different restriction endonucleases have been isolated, which collectively exhibit a few hundred different sequence specificities.

Once a restriction endonuclease encounters its specific recognition sequence on a DNA molecule, it will bind to the DNA molecule and make a cut in one or both of the two sugar-phosphate backbones of the double helix. The positions of this cut/these cuts, if more than one then also the relation to each other, and to the recognition sequence itself, are determined by the identity of the restriction endonuclease. Once the DNA molecule has been cleaved at least one position, it will break into fragments. Restriction endonucleases either cut the DNA backbone symmetrically and leave blunt ends or cleave the DNA backbones in positions that are not directly opposite to each other leading to single-stranded ends (sticky ends). In any case and with the exception of the potential sticky ends, the DNA fragments created by the restriction endonuclease are double-stranded.

Class IIB restriction endonucleases belong to the so-called restriction-modification (R-M) systems of restriction endonucleases which generally comprise two separate proteins, one of which has endonuclease activity and the other one has methyltransferase activity, although in some cases both functions are fused into a single polypeptide. Class II endonucleases cleave DNA at fixed positions in or near their recognition sites. Most need $Mg^{2+}$ as a cofactor. Of the class II enzymes, those of class IIB have bipartite recognition sequences that are usually asymmetric, sometimes palindromic (e.g., in the case of AlfI, BplI and FalI). Class IIB enzymes need AdoMet (S-adenosylmethionine) for DNA methylation and $Mg^{2+}$ for DNA cleavage. The methylation reaction takes place simultaneously to the restriction reaction at the recognition site and the methyl group added prevents subsequent (re-)digestion of the DNA by the particular endonuclease, e.g., after ligating it to another DNA. The positions of DNA cleavage are located at fixed distances upstream and downstream of the enzymes' recognition sites, usually 7 to 15 bases away depending on the enzyme used, resulting in double-strand breaks on both sides of the recognition sites, so cutting a total of four phosphodiester bonds at each site. They release their intact recognition sites from the remainder of the DNA on a short, usually double-stranded fragment, 30 to 38 base pairs long depending on the enzyme. Class IIB restriction endonucleases known so far create 3' overhangs which are 2 to 5 bases long. Exemplary enzymes belonging to type IIB are AlfI, AloI, BaeI, BcgI, BplI, BsaXI, CspCI, FalI, PpiI and PsrI, etc., which are all well-known in the art (see e.g. Marshall et al., 2007, J Mol Biol 367(2): 419-31).

In some embodiments of the present invention, the short DNA fragments comprising the recognition site for said class IIB restriction endonuclease need to be separated from the longer fragments located between said short DNA fragments in the intact DNA molecule. In other words, the DNA fragments comprising the recognition site for said class IIB restriction endonuclease are isolated from the remaining DNA fragments for further analysis. Separation can be effected in multiple ways, the most prominent being separation on an agarose or polyacrylamide gel upon application of an electric field thus separating the fragments according to their size and charge (see e.g. FIG. 2). But separation can also be achieved by size exclusion, e.g. with membranes. After separation by gel electrophoresis, the region on the gel containing the desired fragments comprising the recognition site for said class IIB restriction endonuclease is cut out and treated to elute the fragments with methods well known in the art and described e.g. in Sambrook and Russell, Molecular Cloning, A Laboratory Manual. However, the separation according to step b) is optional (see below for the requirements).

The term "at least one adaptor DNA" relates to single- or double-stranded DNA molecules which are to be attached to DNA fragments. In this regard, single-stranded adaptor DNA(s) are attached to single- or double-stranded DNA fragments, whereas double-stranded adaptor DNA(s) are attached to double-stranded DNA fragments. If more than one adaptor DNA is attached to a DNA fragment, said adaptor DNAs attached to the ends of the DNA fragment can be identical or different.

An adaptor DNA to be attached to the single- or double-stranded DNA fragments serves to prepare the DNA fragments for sequencing, such as high-throughput sequencing comprising $2^{nd}$ generation sequencing techniques. For high-throughput sequencing, the adaptor DNA comprises a sequence which is common for all DNA fragments to be sequenced. For current state of the art $2^{nd}$ generation sequencing technologies, this common sequence serves to anneal the DNA fragments to single-stranded DNA oligonucleotides which are complementary to the common sequence of the adaptor DNA. These single-stranded DNA oligonucleotides are often covalently linked to a solid surface and may serve as sequencing primers. The nature of these oligonucleotides, the solid surface and all subsequent reactions are characteristic for the $2^{nd}$ generation sequencing technology used and well-known in the art.

Attaching an adaptor DNA to DNA fragments comprises techniques such as ligating said adaptor DNA to said DNA fragments or per-base synthesizing nucleotides to the DNA fragments.

Normally, according to the manufacturers protocols of the prior art, e.g. for the Illumina® technique, the attachment of the adaptor DNA to the DNA fragments is effected by ligating the adaptors to one or both 5'- or 3'-ends of the fragments and then optionally carrying out an initial primer extension reaction, in which extension products complementary to the immobilized oligonucleotides are formed. This step optionally comprises an amplification step for multiplying the adaptor-fragment-constructs. For sheared genomic DNA, partially double stranded adaptor DNA (so called forked or y-shaped adaptors) is ligated to both blunt ends of the DNA fragments by a DNA ligase. This can also be effected with DNA fragments created by a class IIB restriction endonuclease in connection with the method of the present invention. Since on one side both strands of the adaptor are non-complementary to each other, the adaptors are y-shaped (=forked): only one side is double stranded and hence able to ligate to the fragments. For use in the present invention, the Y-shaped adaptor DNA comprises one sticky end and is ligated to one or both ends of the double stranded DNA fragments, wherein one strand of the adaptor DNA is ligated to one 5'-end of the DNA fragment and the other strand is ligated to the respective 3' end of the DNA fragment, and this happens on both sides of the DNA fragment. Because the nature (direction and length) but not the sequence of the overhangs created by Type IIB restriction endonucleases are known, the two single stranded DNA molecules forming the Y-shaped adaptor DNA are designed such that, upon pairing of the 2 oligos forming the adaptor, an overhang of all possible DNA sequences at one 3' end is juxtaposed to a phosphorylated 5'-end creating said "sticky end" for efficient ligation to the respective restriction fragments. This overhang consists of a series of "N"s (IUPAC-Code) of appropriate length. The possible presence of remaining and active class IIB restriction endonuclease from the preceding restriction digest reaction does not interfere with the ligation reaction because during digestion, the DNA fragments have been methylated and are thus no longer a substrate for said class IIB endonuclease. After ligating the same forked adaptors to both ends of the double stranded fragments, each resulting DNA strand will have a partially different DNA sequence on its two ends. For RNA samples, such as small RNAs, which are single stranded, ligation of the adaptors is a 2 step process, where first a single stranded RNA molecule is ligated to the 3' end with T4 RNA ligase, then, after a cleanup step, another adaptor RNA is ligated onto the 5' end also with T4 RNA ligase and then the resulting RNA molecules are reverse transcribed, to also arrive at a DNA molecule with adaptors of different sequences on both sides.

The adaptor DNA typically comprises between 20 and 60 nucleotides, possibly containing a DNA barcode.

The sequence common to all adaptors facilitates that the adaptor-fragment construct hybridizes to an oligonucleotide complementary to the sequence common for all adaptors and may serve as the binding site for the sequencing primer. In order to achieve this, the common sequence usually comprises between 15 and 50 nucleotides.

Ligation methods as one technique suitable for attaching adaptor DNA to DNA fragments as described above are well-known in the art (see e.g. Sambrook and Russell, Molecular Cloning, A Laboratory Manual). Exemplary methods utilize ligase enzymes such as DNA ligase such that covalent linkages are formed between the adaptor DNA and the DNA fragment. The adaptor DNA as well as the DNA fragment needs to contain a 5'-phosphate group and a 3'-OH group in order to facilitate ligation of both strands. Ligation takes place by formation of a phosphodiester linkage between the two ends (5' and 3') of polynucleotide strands.

Instead of DNA oligonucleotides, oligonucleotides comprising locked-nucleic-acid bases (LNA©, Exiqon) may be used as part of the adaptor DNA. A locked nucleic acid, often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form of DNA or RNA (see also Koshkin et al., 1998, *Tetrahedron* 54 (14): 3607-30; Obika et al., 1998 *Tetrahedron Lett.* 39 (30): 5401-4.). LNA nucleotides can be used as substitutes for DNA or RNA nucleotides in the oligonucleotide at any desired position. The locked ribose conformation enhances base stacking and backbone pre-organization (Kaur et al., 2006, *Biochemistry* 45 (23): 7347-55). This significantly increases the thermal stability (melting temperature) of oligonucleotides to the complementary strand. In the method of the present invention, one or more, such as two, three, four, five or six LNA bases may be placed in one or both strands of a Y-shaped adaptor DNA, as well as in any double-stranded adaptor or single stranded oligonucleotide, such as those applied in the fourth aspect of the invention described further below to greatly increase the binding energy and hence make DNA-DNA interactions more stable.

After ligation, the ligation products may be purified from remaining components of the ligation reaction such as enzymes, buffers, salts, unligated components etc. using methods well-known in the art.

Step (c) serves to attach the DNA fragments to the adaptor DNA.

The term "adaptor-fragment construct" describes a construct comprising a DNA fragment and one or two adaptors attached (i.e., ligated and/or synthesized) to one or both ends of said DNA fragment. The resulting construct may accordingly have a structure "adaptor-fragment", "adaptor-fragment-adaptor" or "fragment-adaptor".

The method of the invention may optionally comprise a step of denaturing the DNA fragments obtained in step b) prior to step c). Denaturing the DNA fragments results in single-stranded DNA fragments to which single-stranded adaptor DNA may be attached in step c).

Sequencing techniques suitable in the method of the present invention include techniques well-known in the art as $2^{nd}$ generation sequencing techniques, comprising any solid phase technique wherein nucleotides are added successively to a 3' hydroxyl group resulting in the synthesis of a polynucleotide chain in 5' to 3' direction ("Sequencing by Synthesis"). Currently these techniques operate on prepared DNA libraries where the DNA to be sequenced has specific adaptors attached to the ends. Besides the specific methods described herein, the present invention in general makes use of class IIB restriction endonucleases in $2^{nd}$ generation sequencing methods.

Alternative high-throughput sequencing techniques applicable in the method of the invention include Pyrosequencing TM, FISSEQ (fluorescent in situ sequencing), MPSS and sequencing by ligation methods. Another alternative is of course traditional Sanger sequencing.

It is to be understood that not necessarily all DNA fragments obtained in step b) and/or c) are sequenced. This is largely due to losses of fragments in each step of the method of the invention or due to the limited capacity of the sequencing device. In any case, it is attempted to sequence as many DNA fragments as possible. The fraction or number of DNA fragments necessary to sequence can readily be determined by the person skilled in the art. It depends on the application e.g., on the size of the genome examined, the number of individuals/samples, the size of the DNA library, and/or, if used, the number of barcodes (which will be described in detail further below). For most applications it is meaningful to sequence as many fragments as needed to have each of the theoretically expected (or predicted) fragments sequenced several times, where "several times" is a sufficient number to unambiguously determine its sequence (including a possibly attached barcode) given the error rate of the sequencing technique. In this regard, the term "at least a fraction" relates to the above minimal number of DNA fragments to be sequenced. The term does not relate to the partial sequencing of the DNA fragments resulting in sequence reads shorter than the length of the DNA fragments.

Once the DNA fragments have been sequenced from one end, they may be further analysed by obtaining a sequence read from the opposite end of the fragment. For second generation techniques such as the Illumina® technique, depending on the approach taken, this is either the end of the fragment which was not initially immobilized on the surface or the end which was initially immobilized on the surface.

The term "assigning a genotype" refers to the evaluation of the sequence data obtained in step (d). The term includes the comparison of the sequences detected with those of a reference sample as described below to analyse, e.g., for polymorphisms such as SNPs. If one or more polymorphisms are found, one may conclude that a certain genotype is present in the sample analysed. Different genotypes can be present e.g., in individuals of the same species which are situated in the same or a different environment.

The present inventors have found a way to obtain comparable sequence information from samples of different sources, which results in a reduction of the sequencing effort to less than 5%, depending on the sample used even to less than 1%.

Commonly applied sequencing techniques use short fragments of different samples (which can be barcoded) which are completely sequenced. The fragments of each sample are obtained by randomly fragmenting the DNA samples using e.g., a nebulizer. In doing this, any information regarding the position of a fragment within the DNA sample is lost unless sufficient overlapping fragments are completely sequenced and assembled.

The present method relies on defined, non-random DNA fragments generated using a class IIB restriction endonuclease. As apparent from FIG. 1 on the example of the class II restriction endonuclease AflI, recognition sites for class II enzymes are evenly distributed in genomes such as that of *A. thaliana*. In this particular example sequencing all ~3100 AflI restriction fragments would represent a defined subset of the DNA sequence of Chromosome 1.

Figure 4:
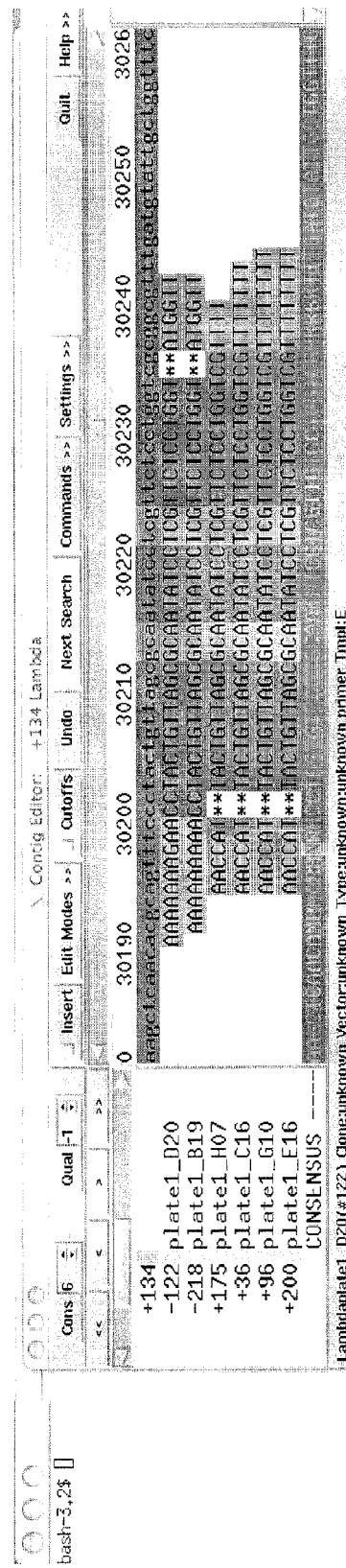
Figure 4:
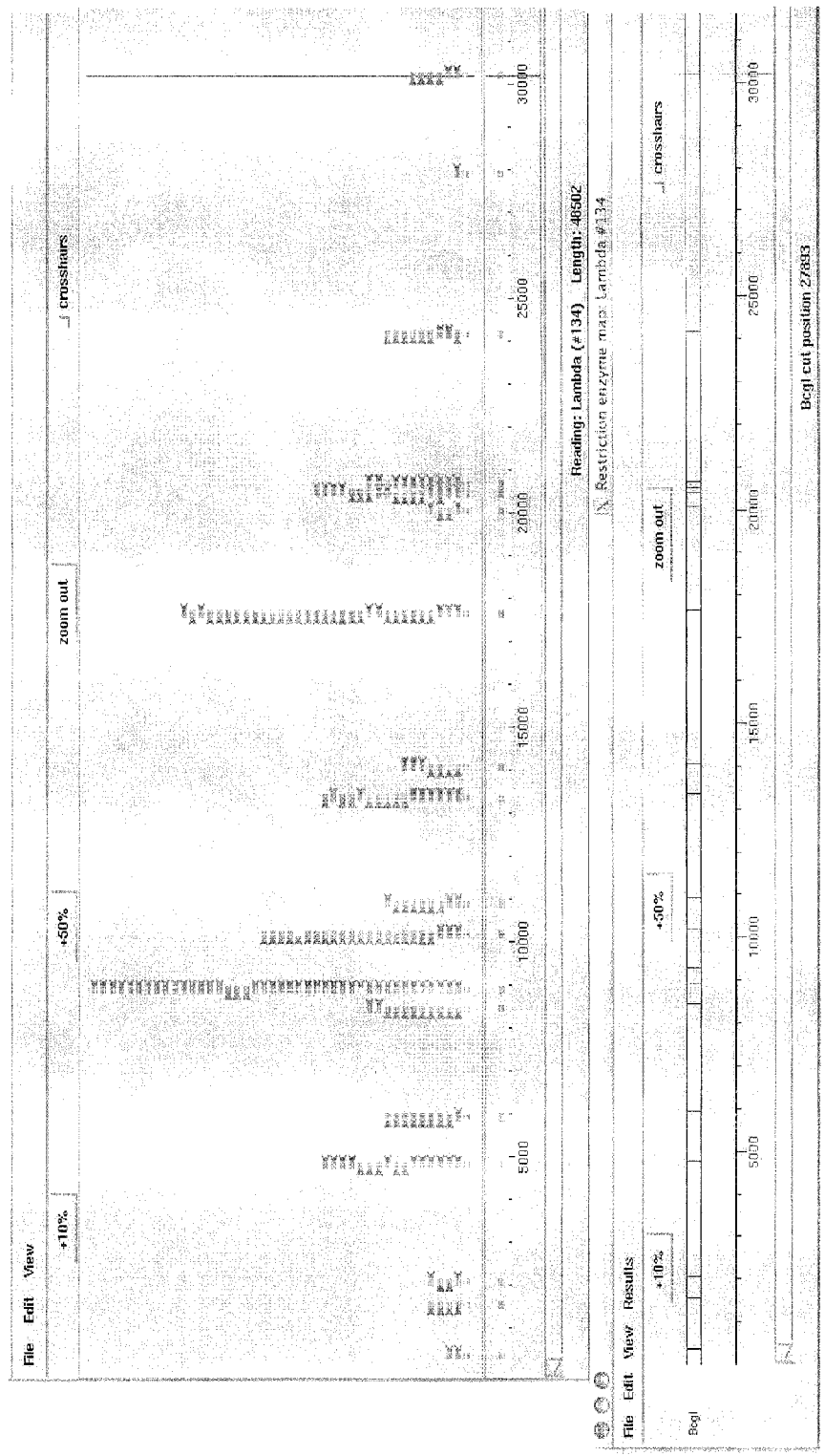
Figure 4:
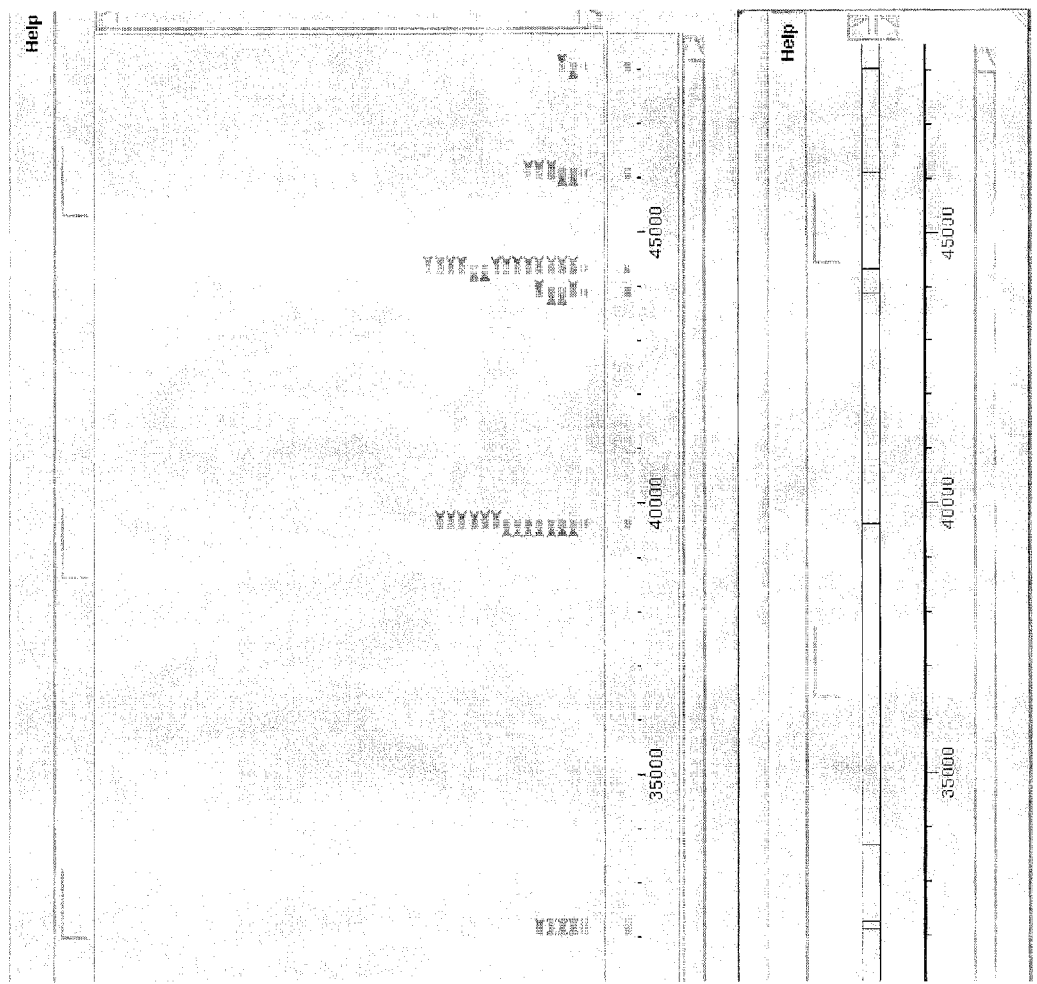

The present inventors have applied the present method and found that the sequence information contained in the fragments created and sequenced are sufficient to enable for assigning a genotype to a DNA sample (see FIG. 4). In this regard, the number of fragments to be analysed is greatly decreased thus significantly reducing the effort to arrive at useful data. Furthermore, as compared to methods using restriction enzymes other than class IIB enzymes, the sequence read can be verified by determining the sequence from both ends of the fragments, because the fragments are short and of defined, uniform length. This enhances the quality of the reads and of the data to be processed. In addition, the fragments contain a well-defined sequence motif (the complete recognition site of the restriction enzyme used) approximately in the middle of the fragments. The desired fragments are therefore easy to recognize post sequencing and easily distinguished from contaminations, that is, accidentally acquired DNA sequence from other regions of the genome; again enhancing quality.

In a preferred embodiment, said at least one DNA sample is a plurality of DNA samples and said adaptor DNA attached in c) (i) comprises a DNA barcode specific for each DNA sample; or (ii) is amplified using at least one primer binding to said adaptor DNA, wherein said primer comprises a DNA barcode specific for each DNA sample; and step e) further comprises determining the sequence of the DNA barcode specific for each sample.

Depending on the respective embodiment of the invention, the primers used for amplification can be universal for all adaptor-fragment strands or they (forward or reverse primer or both) carry unique sequence, e.g., barcode sequences that denote the source of the nucleic acid sample the fragment was obtained from.

This embodiment of the present invention enables for the parallel sequencing of a large number of fragments of different DNA samples.

A barcode is a detectable representation of data containing information about the object the barcode is contained in. In connection with the present invention, a barcode refers to a DNA barcode. Such barcode providing information about a DNA sample is attached to each of the DNA fragments arising from digestion of one DNA sample and comprising the above-mentioned recognition site prior to the sample fragments being sequenced.

The DNA barcode is a nucleic acid strand of nucleotides in a particular order, and different barcodes are different combinations of nucleotides. The length of the barcode determines the coding capacity (that is, how many different samples can be distinguished post sequencing). However, since practical sequencing read length by $2^{nd}$ generation sequencing techniques is limited, short DNA barcodes are preferred. Hence, while meaningful barcodes of any lengths could be used, they are preferably between 4 to 15, more preferably between 4 to 10 and most preferably between 4 and 8, such as 4, 5, 6, 7 or 8 nucleotides long. Ideally, the barcodes are designed such that they can be unambiguously called post sequencing, even if sequencing mistakes have occurred. The length of the barcode attached to the fragments of one nucleic acid sample may vary. In this case the respective adaptor molecules comprising said barcode are otherwise identical in order to enable for the unambiguous identification of the barcode sequence and the DNA fragment, respectively.

In a preferred embodiment, step e) comprises comparing the sequence data of said at least one DNA sample with those of a reference DNA sample and analysing for differences in the nucleic acid sequence, e.g. in the form of nucleotide polymorphisms, of at least one DNA fragment of said at least one DNA sample analysed as compared to said reference DNA.

The reference sample may be a DNA sequence which has been determined previously. The sequences of the DNA fragment sequences may be aligned with the sequence of the reference sample by computer-based methods. To evaluate the identity level between two DNA sequences, they can be aligned electronically using suitable computer programs known in the art. Such programs comprise BLAST (Altschul et al., J. Mol. Biol. 1990, 215: 403), variants thereof such as WU-BLAST (Altschul & Gish, Methods Enzymol. 1996, 266: 460), FASTA (Pearson & Lipman, Proc. Natl. Acad. Sci. USA 1988, 85: 2444) or implementations of the Smith-Waterman algorithm (SSEARCH, Smith & Waterman, J. Mol. Biol. 1981, 147: 195). These programs, in addition to providing a pairwise sequence alignment, also report the sequence identity level (usually in percent identity) and the probability for the occurrence of the alignment by chance (P-value). The BLASTN program for nucleic acid sequences uses as default a word length (W) of 11, an expectation (E) of 10, M=5, N=4, and a comparison of both strands. Programs such as CLUSTALW (Thompson Nucl. Acids Res. 2 (1994), 4673-4680) can be used to align more than two sequences. In addition, CLUSTALW, unlike e.g. FASTDB, does take sequence gaps into account in its identity calculations.

All of the above programs can be used in accordance with the invention.

Alternatively, the reference sample has been treated in the same way to yield the same type of fragments. Preferably, the sequence of not only the fragments but also the complete nucleic acid forming the sample is known so that the assignment of a position of a certain fragment within the nucleic acid is possible.

In a preferred embodiment of the method of the invention, wherein more than one DNA samples are analysed, step e) comprises comparing the sequence data of the DNA samples forming said plurality of DNA samples with each other and analysing for differences in the nucleic acid sequence, e.g., in the form of nucleotide polymorphisms, of at least one DNA fragment of at least one DNA sample analysed.

In this embodiment, no comparison with a reference DNA is necessary since genotyping is effected within the samples analysed. In other words, if a plurality of DNA samples is analysed each of said samples may serve as a reference sample for one or more other samples.

In another preferred embodiment, said genotyping comprises haplotyping.

Systematic studies of common genetic variants are facilitated by the fact that individuals who carry a particular SNP allele at one site often predictably carry specific alleles at other nearby variant sites. This correlation is known as linkage disequilibrium (LD); a particular combination of alleles along a chromosome is termed a haplotype. Thus the term "haplotyping" refers to the determination of haplotypes of a sample.

In a different aspect, the present invention relates to a method for physical mapping, i.e., determining the position of DNA molecules comprised in a DNA library relative to each other within the DNA sequence represented by said DNA library and/or within a known DNA sequence, comprising: (a) digesting DNA molecules comprised in a DNA library with a class IIB restriction endonuclease to generate DNA fragments; (b) optionally separating DNA fragments comprising the recognition site for said class IIB restriction endonuclease from the remaining DNA fragments; (c) attaching at least one adaptor DNA to the 5' and/or 3' end of one or both strands of the DNA fragments comprising the recognition site for said class IIB restriction endonuclease obtained in a) or separated in b) to form adaptor-fragment constructs; (d) determining the sequence of at least a fraction of the DNA fragments obtained in c); (e) analysing for overlapping sequences between the DNA fragments sequenced in d); (f) allocating a position to said DNA fragments relative to each other and within the DNA sequence represented by said DNA library based on the sequence overlaps identified in e) and/or (g) allocating a position to said DNA fragments relative to each other and/or within a known DNA sequence.

A "DNA library" is a collection of a cell's or an organism's genetic information that are stored in vectors within a host organism and is often used in the arts. For this purpose the respective genetic/genomic information contained on one or more chromosomes or corresponding to transcribed genetic/genomic information (in the form of cDNA) is cut or sheared into fragments by one or more restriction endonucleases or physical force and then usually inserted into a suitable vector. Each individual vector molecule containing a piece of the source organism's DNA is then transformed into a separate host organism, usually microorganisms such as bacteria (e.g., *E. coli*) or fungi, (e.g., yeast (*S. cerevisiae*)), for amplification and storage. The entirety of host organisms transformed with vectors comprising the fragments of one cell's or organism's genetic/genomic information (e.g., their DNA) forms the DNA library. If restriction endonucleases are used, a library is often built using genetic material digested with different sets of restriction endonucleases and combining the fragments obtained with each combination of enzymes, or by incomplete digestion using a single enzyme. This results in fragments overlapping each other and a specific sequence comprised in the genetic/genomic information is represented on distinct and different fragments more than once in the library, given the number of fragments is sufficiently large. The same is true when the DNA has been physically sheared prior to insertion into the vectors. The genome size of the source organisms as well as the insert sizes determines the number of individual clones needed to completely represent the genome of the source organism. Libraries prepared from genomic DNA and stored in host bacteria are often BAC (Bacterial Artificial Chromosome) libraries or Fosmid/Cosmid libraries.

In connection with this aspect of the present invention, suitable libraries are preferably those, wherein the DNA sequence represented in the library is a contiguous DNA sequence. Such a contiguous strand can be e.g., a chromosome. If more than one contiguous DNA strand such as more than one chromosome of an organism are represented in a library, said library can be used to determine the position of DNA molecules comprised in a DNA library relative to each other within one contiguous DNA strand represented by said DNA library. Libraries representing more than one DNA strand can in any case be used to determine the position of said DNA molecules within a known DNA sequence.

A vector is a DNA molecule used as a vehicle to transfer foreign genetic material—as insert—into another cell. The four major types of vectors are plasmids, bacteriophages and other viruses, cosmids, and artificial chromosomes. Common to all engineered vectors are an origin of replication, a multicloning site, and a selectable marker.

Artificial chromosomes are scaffold nucleic acids containing inserts of foreign nucleic acids. Examples of artificial chromosomes are bacterial artificial chromosomes (BACs) and yeast artificial chromosomes (YACs). A YAC is a vector used to clone large DNA fragments (larger than 100 kb and up to 3000 kb). Other yeast vectors are YIps (yeast integrating plasmid), and YEps (yeast episomal plasmid). A bacterial artificial chromosome (BAC) is a DNA construct, based on a fertility plasmid (or F-plasmid), used for transforming and cloning in bacteria, usually *E. coli* F-plasmids play a crucial role because they contain partition genes that promote the even distribution of plasmids after bacterial cell division. The bacterial artificial chromosome's usual insert size is 150-350 kbp, but can be greater than 700 kbp. A similar cloning vector called a PAC has also been produced from the bacterial P1-plasmid. A cosmid is a type of hybrid plasmid (often used as a cloning vector) that contains cos sequences, DNA sequences originally from the Lambda phage. Cosmids can be used to build genomic libraries and are able to contain 37 to 52 kbp of DNA, while normal plasmids are able to carry only 1 to 20 kbp.

Preferred libraries are BAC- and YAC-libraries.

The number of DNA molecules comprised in a DNA library which is digested in step a) depends, inter alia, on the DNA library used (insert size) and the extent of the genetic/genomic information contained within said library. The longer the sequence comprised in said library, the more clones carrying parts of said sequence, in connection with this and the following embodiment also referred to as "DNA molecules", it comprises. Accordingly, in order to ensure that the complete sequence is covered by the number of DNA molecules chosen, the coverage of the sequence as well as its length needs to be taken into account. Usual coverages of DNA libraries lie between 3 and 20-fold, but can deviate depending on their purpose. For example, a plant genome such as that of maize is about 3 MB long and among others, there is a HindIII library of 247,680 clones, ZMMBBb, constructed at Clemson University Genomics Institute (CUGI) in 2005, that has an average insert size of 137 kB which results in a genome coverage of ~17×. (Coe and Schaeffer. Genetic, physical, maps, and database resources for maize. Maydica (2005) vol. 50 (¾) pp. 285).

The number of DNA molecules to be digested is determined depending on purpose and library by a person skilled in the art. In general at least 2-3 fold, more preferred 5-10 fold genome coverage should be aimed at. In other words, taking all DNA molecules to be digested together, each nucleotide position in the genome should be represented 2-10 times. At the same time, each fragment obtained in step (b) of the main embodiment is preferably sequenced several times on average. Accordingly, the fraction of the DNA fragments as recited in step (d) of the main embodiment is preferably chosen such that the above defined coverage is obtained.

In case the position of DNA molecules within a known DNA sequence is to be determined, a sufficient number can be as low as one molecule if it contains a class II restriction site since the sequence of the fragments obtained after digesting said molecules can be aligned to the known DNA sequence.

After sequencing the fragments, they are analysed for sequences found in more than one fragment. Given the length of the Type II fragments, with above 30 bp, the vast majority of them can be regarded as unique within the cell's or organism's genetic/genomic information. With this information, it is possible to allocate a position to the DNA fragments analysed relative to each other and within the DNA sequence represented by the DNA library. Alternatively or in addition, in case the sequence identity is sufficiently high, the position of said fragments within a DNA sequence which is not represented by the DNA library but is homologous to it may be allocated. This allows for comparison of so far unsequenced DNA libraries with existing sequenced genetic/genomic data.

In a preferred embodiment of the first and second aspect, more than one class IIB restriction enzymes are used in step a). Accordingly, in connection with the present invention, the term "a class IIB restriction endonuclease" also means "at least one class IIB restriction endonuclease" such as at least 2, at least three, at least four class IIB restriction endonucleases. If more than one class IIB restriction endonuclease is used for digesting DNA molecules, more fragments comprising the recognition site of the restriction endonucleases used are obtained resulting in higher sequence coverage of the DNA sample. As discussed above, recognition sites of specific class IIB restriction endonuclease are evenly distributed within DNA sequences. Accordingly, more than one restriction endonuclease applied in digesting DNA molecules would result in more fragments to be sequenced which, depending on the composition of the DNA molecules contained in the DNA sample, could further facilitate sequence determination and the assignment of genotypes, the latter in particular since further differences in the at least one DNA sample analysed can be retrieved leading to a more detailed characterization of genotypes.

In another preferred embodiment of the first and second aspect, the method further comprises, after step c) and prior to step d), amplifying said adaptor-fragment constructs. This step serves to render the DNA fragments obtained after digestion and separation double-stranded and to amplify them. Methods for amplification are well-known to the skilled person and include methods such as PCR. PCR is employed to make large numbers of copies of a target sequence. This is done on an automated cycler device, which can heat and cool containers with the reaction mixture in a very short time. The PCR, generally, consists of many repetitions of a cycle which consists of: (a) a denaturing step, which melts both strands of a DNA molecule and terminates all previous enzymatic reactions; (b) an annealing step, which is aimed at allowing two primers to anneal specifically to the melted strands of the DNA molecule; and (c) an extension step, which elongates the annealed primers by using the information provided by the template strand. Generally, PCR can be performed for example in a 50 µl reaction mixture containing 5 µl of 10×PCR buffer with 1.5 mM $MgCl_2$, 200 µM of each deoxynucleoside triphosphate, 0.5 µl of each primer (10 µM), about 10 to 100 ng of template DNA and 1 to 2.5 units of Taq polymerase. The primers for the amplification may be labeled or be unlabeled. DNA amplification can be performed, e.g., with a model 2400 thermal cycler (Applied Biosystems, Foster City, Calif.): 2 min at 94° C., followed by 30 to 40 cycles consisting of annealing (e.g. 30 s at 50° C.), extension (e.g. 1 min at 72° C., depending on the length of DNA template and the enzyme used), denaturing (e.g. 10 s at 94° C.) and a final annealing step at 55° C. for 1 min as well as a final extension step at 72° C. for 5 min. Suitable polymerases for use with a DNA template include, for example, *E. coli* DNA polymerase I or its Klenow fragment, T4 DNA polymerase, Tth polymerase, Taq polymerase, a heat-stable DNA polymerase isolated from *Thermus aquaticus* Vent, Amplitaq, Pfu and KOD, some of which may exhibit proof-reading function and/or different temperature optima. However, the person skilled in the art knows how to optimize PCR conditions for the amplification of specific nucleic acid molecules with primers of different length and/or composition or to scale down or increase the volume of the reaction mix.

The maximum length of DNA fragments amplified in a PCR reaction can be controlled by the extension time. Using a very short extension time, the desired short fragments (30-38 bp) carrying the recognition site for the class MB restriction endonuclease but not the longer DNA fragments in between said DNA fragments are amplified. In the case of such short extension times, a separation step according to step b) of the method of the first and second aspect or a step d) according to the third aspect below may be omitted. In other words, if an amplification step with a short extension/amplification time is present in any of the methods according to the first, second or third aspect (see below) of the invention, such as an amplification to introduce a DNA barcode according to step c)(ii) of the first and second aspect or step e)(ii) of the third aspect, or an amplification after step c) of the first and second aspect or after step e) of the third aspect. Accordingly, a short amplification/extension time that could make a separation step unnecessary would be 10 min or less, preferably 5 min or less, more preferably 4 min or less, such as three min or less, 2 min or less, 1 min or less, 30 s or less or 15 s or less.

If the adaptor DNA attached in step c) (or step e) of the third aspect described below) does not contain a DNA barcode and is amplified using at least one primer binding to said adaptor DNA, wherein said primer comprises a DNA barcode specific for each DNA sample, both this amplification step and that described above can be combined in one step.

In another preferred embodiment of the first and second aspects of the invention, the method further comprises immobilising the adaptor-fragment-constructs obtained in step (c) on a solid surface prior to step (d).

Immobilization is preferably effected by base-pairing of a portion of the adaptor DNA with oligonucleotide primers complementary to said portion which are already immobilized on a solid surface. The immobilized primers can be a lawn on a planar surface or on a pool of beads. The method of the present invention preferably utilizes solid phase PCR or solid phase isothermal amplification which are characterized by one or both primers being immobilized on a solid surface. Both primers may be identical and determined by the common sequence in the adaptor DNA. They may also be different if a method of the invention described further below is used.

The primers for solid phase amplification can be immobilized by single point covalent attachment to the solid surface at or near the 5' end of the primer, leaving the template specific portion of the primer free to anneal to its cognate template and the 3' hydroxyl group free for primer extension. The kind of attachment depends on the nature of the solid surface and potential derivatisation or functionalization of said surface. The primer may include a moiety which may be a non-nucleotide chemical modification to facilitate attachment. Examples of such modifications are sulfur-containing nucleophiles such a phosphorothioate or thiophosphate at the 5' end.

The solid surface has been prepared to have oligonucleotide primers attached to it which are complementary to a portion of one or both adaptors. When applying the adaptor fragment constructs to the solid surface, the complementary portions of the adaptor DNAs bind to the oligonucleotide primers attached to the solid surface and are thus immobilized. Where both forward and reverse primers complementary to portions of the adaptor DNA are immobilized on the solid surface, annealing of an adaptor fragment construct comprising two adapters causes the formation of bridged structures.

The solid surface applied in the present invention is composed of an inert substrate or matrix such as glass, silica or plastic slides or polymer beads. The surface may be derivatized with a chemical compound or composition providing reactive groups which permit covalent attachment to nucleic acids such as DNA. The nucleic acid may itself be non-covalently or, preferably, covalently attached to the surface. Non-limiting examples of such surfaces are polyacrylamide hydrogels applied on glass. In turn, the nucleic acids will be covalently attached to the reactive groups provided by the compound or composition applied to the solid surface.

Immobilization enables for advanced sequenced techniques such as the Illumina® technique.

In another preferred embodiment of the first and second aspect of the present invention, the method further comprises immobilising said adaptor DNA to be attached to the DNA fragments in step c) to a solid surface prior to step c).

In this embodiment, the DNA molecules are immobilized to increase efficiency and to ease cleanup between the reaction steps. This can be achieved e.g., by using a primer blocked at the 5'-end as will be described in connection with the method of the invention for attaching different DNA adaptors to the 3' and the 5' end of a DNA molecule (see step (b)), e.g., carrying a Biotin on the 5' end and binding it to a Streptavidin coated surface prior to b) or c). Accordingly, immobilization according to this embodiment is to be held distinct from the immobilization step described further above which is to be performed after step (c) and prior to step (d) of the main embodiment and which serves to permit sequencing with, e.g., the Illumina® sequencing technique.

In another preferred embodiment, said adaptor-fragment constructs of all DNA samples are pooled prior to immobilization and sequencing. Pooling means that the adaptor-fragment constructs of all samples are assembled or mixed.

In a more preferred embodiment of the first and second aspect, the method further comprises amplifying said adaptor-fragment constructs immobilised after step c) on said solid surface prior to step d).

This additional amplification step serves for enhancing the sensitivity of the sequencing method. After immobilization to the solid surface, the adaptor-fragment constructs are amplified by conducting a solid phase PCR reaction as described above.

In another preferred embodiment of the second aspect, the method further comprises determining the minimum tiling path of the DNA library after step f).

Completely sequencing all DNA fragments obtained from an aforementioned DNA library would yield the entire genome sequence of the source organism, but in 10 or more fold coverage (depending on the size of the library and the genome coverage it represents), which would be cost intensive. It is therefore preferred that only a subset of these clones is sequenced to achieve an overall sequence coverage of 1 to 2-fold. In other words, in order to avoid the necessity of sequencing all existing clones of a DNA library, it is desirable to first determine a minimal "tiling path", that is, a subset of these clones that together span the genome once with sufficient overlap between them, followed by sequencing only these clones belonging to this minimum tiling path.

Every clone, e.g. on said minimal tiling path, can be sequenced as a separate project thus keeping the computing problems within reasonable bounds and avoiding most problems concerned with large scale duplications, an advantage especially in large, repetitive genomes like maize, etc.

The subset of clones representing a minimum tiling path is usually selected after all clones belonging to a library are assembled relative to each other. The most commonly used technique at present is "library fingerprinting": Each individual clone's (e.g. BAC clone's) DNA is isolated, digested with restriction endonucleases, the resulting pattern of fragment sizes is determined by gel electrophoresis and subsequently the overlap of clones with each other and thus the relative order is inferred by shared patterns (fragments of the same size) between the clones.

The method of the present invention also allows for optimally assembling all clones in a library relative to each other, since clones that overlap will share the same fragment sequences determined with the method of the present invention. It is then, subsequently, possible to minimize the number of clones to be used to cover the complete DNA sequence represented by a DNA library simply by selecting one "minimum tiling path".

In a third aspect the present invention relates to a method for establishing a cross-reference between individual DNA molecules and their location in an at least three dimensional matrix, the method comprising: (a) distributing DNA molecules comprised in a library in an at least three-dimensional matrix comprising multiple distinct locations in all of said at least three dimensions such that each DNA molecule is contained in one of said locations; (b) combining the DNA molecules into different pools, such that each DNA molecule is present in at least three different pools; (c) digesting the DNA fragments contained in each pool with a class IIB restriction endonuclease to generate DNA fragments; (d) optionally separating DNA fragments comprising the recognition site for said class IIB restriction endonuclease from the remaining DNA fragments for each pool; (e) attaching at least one adaptor DNA to the 5' and/or 3' end of one or both strands of the DNA fragments comprising the recognition site for said class IIB restriction endonuclease obtained in c) or separated in d) to form adaptor-fragment constructs and optionally amplifying said adaptor-fragment constructs; wherein said adaptor DNA (i) comprises a DNA barcode specific for each pool; or (ii) is amplified using at least one primer binding to said adaptor DNA, wherein said primer comprises a DNA barcode specific for each pool; and (f) determining the sequence of at least a fraction of the DNA fragments obtained in e) and the sequence of the DNA barcode attached thereto; and (g) cross-referencing all individual DNA molecules to their locations within said at least three-dimensional matrix based on the sequence data obtained in f), wherein the location of each individual DNA molecule is determined as the point of intersection of said at least three pools it is comprised in.

An at least three dimensional matrix according to the present invention comprises multiple distinct locations in all at least three dimensions. Examples of three-dimensional matrices are e.g. assemblies formed by stacked multi-well plates, where row, column and plate represent the 3 dimensions. More than three dimensions can be achieved by e.g., combining them in additional, different combinations or in other/different three-dimensional matrices. Another preferred pooling strategy is based on the Chinese Remainder Theorem as detailed in Erlich et al. Genome Res (2009) vol. 19 (7) pp. 1243-53.

The term "combining the DNA molecules in different pools" refers to the assembly of the DNA molecules comprised in the matrix in different combinations. For example, within an assembly comprising stacked multi-well plates, pools may be formed of each horizontal row of all multi-well plates in the stack determining the x axis of the matrix, of each vertical row (column) of all multi-well plates determining the y-axis of the matrix and of each plate, determining the z axis of the matrix. Any other combination of the DNA molecules in said distinct locations is possible as long as the position of each single DNA molecule within the matrix can be unambiguously determined by combining the information obtained from the at least three different pools.

When digesting the DNA fragments in step c) of the third aspect, the pools are kept separate from each other. Each pool forms a sample to be analyzed.

The DNA barcode attached to each DNA fragment characterizes its origin and allocates them to a pool.

As has already been described for step a) of the first and second aspects of the present invention, more than one class IIB restriction endonucleases can be used in step c).

In a preferred embodiment of the third aspect, the DNA fragments comprising the recognition site for said class IIB restriction endonuclease obtained in step (d) are denatured prior to step (e).

In a further preferred embodiment of the third aspect of the invention, the method further comprises immobilising the adaptor-fragment-constructs obtained in step (e) on a solid surface prior to step (f).

In a more preferred embodiment, the method further comprises amplifying said adaptor-fragment strands immobilised prior to step f) on said solid surface.

This step is carried out and serves the same purpose as described above for the first and second aspects.

In another preferred embodiment of the third aspect of the present invention, the method further comprises immobilising said adaptor DNA to be attached to the DNA fragments in step e) to a solid surface prior to step e).

In this embodiment, as has been described above, the DNA molecules are immobilized to increase ligation efficiency and to ease cleanup between the reaction steps.

In a more preferred embodiment of the second and third aspect, said adaptor-fragment constructs of all DNA samples are pooled prior to immobilization and sequencing.

In another preferred embodiment of the third aspect, the method further comprises determining the minimum tiling path of the DNA library after step (g).

In a further preferred embodiment of the invention, said determining of the sequence is effected starting from both ends of the adaptor-fragment constructs.

In a further, fourth aspect, the present invention relates to a method for attaching different DNA adaptors to the 3' and the 5' end of a DNA molecule comprising: (a) attaching a poly-dNTP strand terminated by ddNTP to the or each 3' end of a single- or double-stranded DNA molecule, wherein all dNTPs are the same and wherein N in ddNTP is not N in dNTP; (b) annealing a primer comprising a 3' poly-dNTP strand complementary to the poly-dNTP strand attached in a), wherein the N in the 3' terminal dNTP is different from the N of the remaining poly-dNTP strand, to the nucleic acid strand of b), wherein the 5' end of said primer is blocked; (c) removing the unpaired nucleotides of the poly-dNTP strand produced in a) and filling-in the 3' ends of both DNA strands to form blunt ended double stranded DNA fragments; (d) adding a dNMP to the 3' end of each DNA strand; (e) ligating to each double strand having a 3' dNMP overhang and a 5' phosphate a double stranded DNA adaptor having a 3' dNMP overhang complementary to the 3' overhang of said double strand; and, optionally, (f) amplifying the DNA obtained in e).

The "N" as used in connection with "dNTP" or "ddNTP" in the present invention relates to one of the four bases forming the genetic code, i.e. adenine, cytosine, guanine or thymine, alternatively also uracil.

The dNTP strand attached in step (a) is single-stranded and forms a homopolymer comprising a sequence of only one base. Said homopolymer is terminated by a ddNTP at its 3'-end which is a base different from that of the homopolymer.

The term "attaching a poly-dNTP strand" in connection with this aspect of the present invention can be effected either by ligating a complete dNTP strand of the desired length or by synthesising and attaching each single dNTP subsequently.

The number of 3'-ends comprised in a DNA molecule depends on whether said molecule is single- or double-stranded. Accordingly, a single-stranded DNA molecule has only one 3'-end, whereas a double-stranded DNA molecule has two 3'-ends on opposite sites of the molecule.

LNA bases (Exiqon©) may be used in connection with each oligonucleotide or primer applied in any aspect of the present invention, such as the primer applied in step b) and/or the poly-dNTP strand of the fourth aspect. One or more LNA bases are preferably introduced into oligonucleotides or primers which will form part of a double-strand at a later stage. Accordingly, any one of said oligonucleotides or primers, such as the primer applied in step b) and/or the poly-dNTP strand of the fourth aspect, may comprise one or more, such as two, three, four, five or six LNA bases (Exiqon©).

Figure 3:
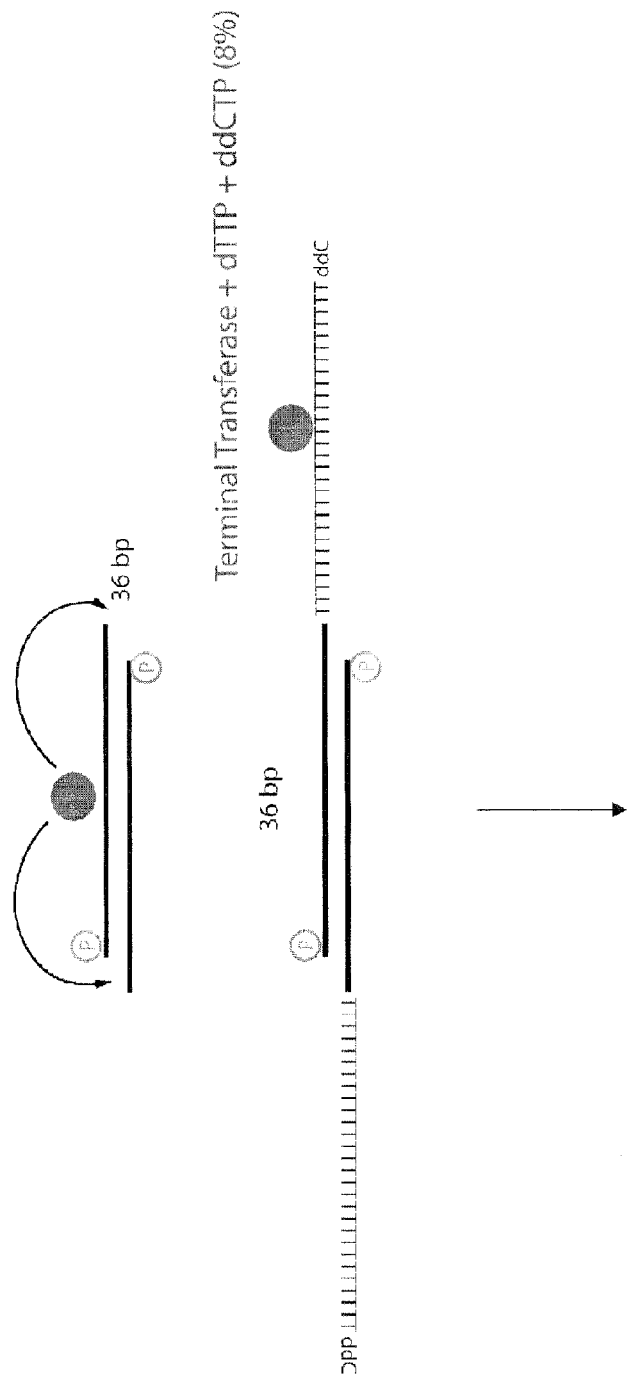
Figure 3:
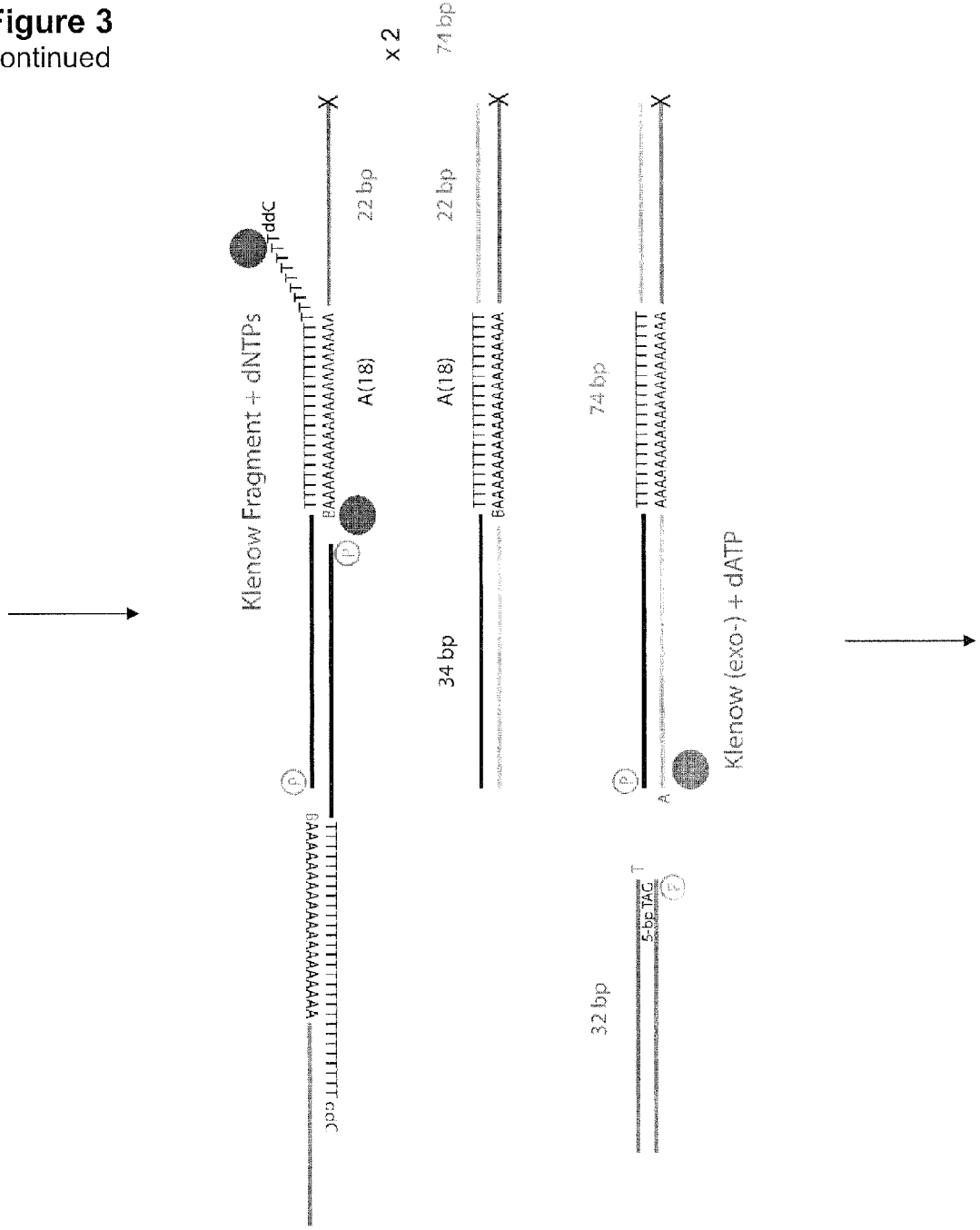
Figure 3:
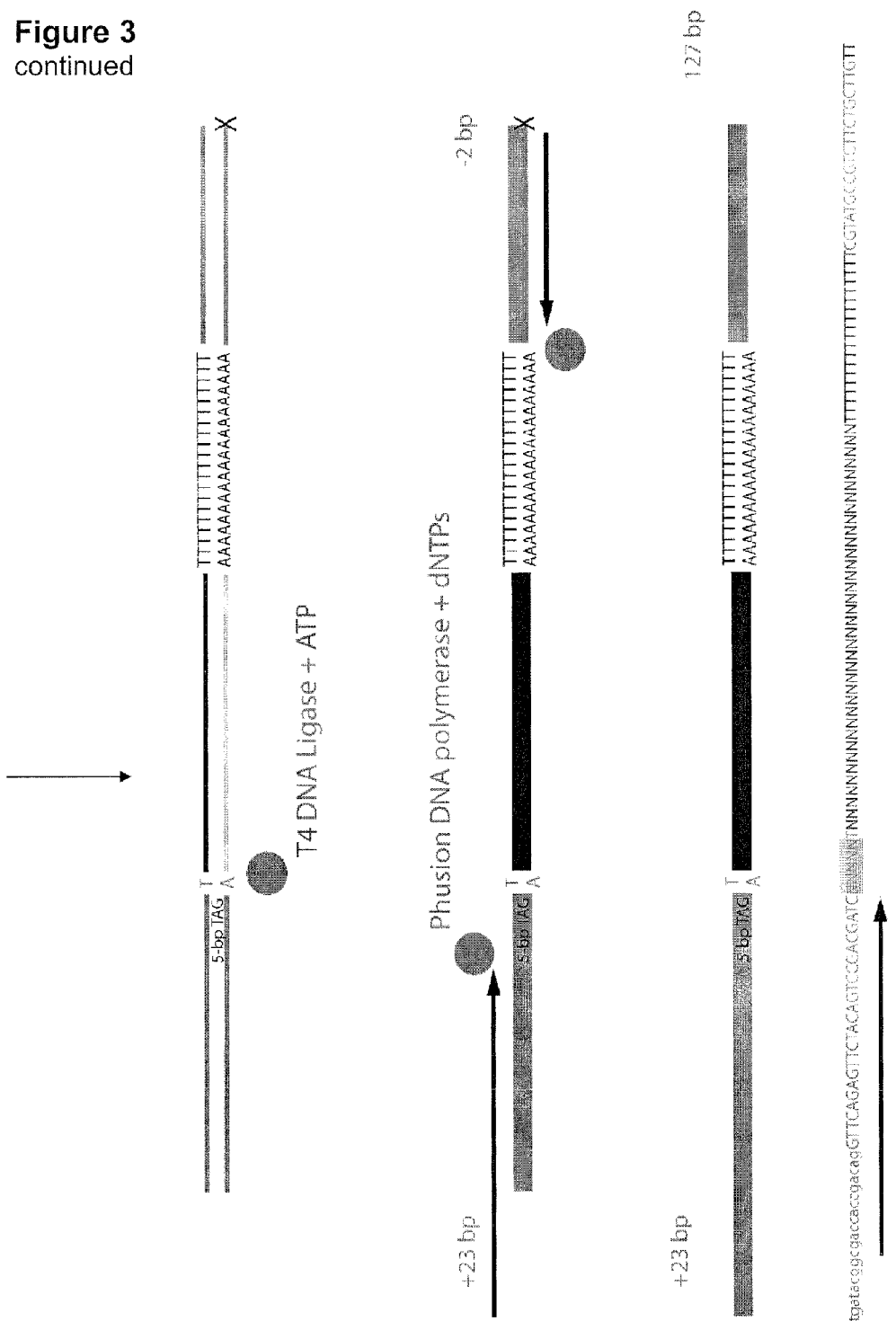

The sequence of the method of the present invention is also depicted in FIG. 3.

In a preferred embodiment, in the case that double-stranded DNA molecules are provided in step a), these are dissociated prior to step b).

In a preferred embodiment, the DNA adaptor ligated in step (e) further comprises a barcode sequence.

In a preferred embodiment of the first, second and third aspect of the invention, said attaching of the adaptor DNA is carried out using the method according to the method for attaching different DNA adaptors to the 3' and the 5' end of a DNA molecule of the invention. Such adaptors may comprise one or more, such as two, three, four, five or six LNA bases (Exiqon©).

In another preferred embodiment of the first, second and third aspect of the invention, said attaching of the adaptor DNA is carried out using a Y-shaped adaptor DNA as described above, optionally comprising one or more such as two, three, four, five or six LNA bases (Exiqon©) in one or both strands. For this attachment, ligation of the adaptor DNA is effected as described above, optionally followed by an amplification step of the resulting adaptor-fragment constructs as also described above.

The present invention furthermore relates to a kit comprising the enzymes necessary to perform the method of the invention. An exemplary set of such enzymes comprises one or several Type IIB restriction enzymes, Terminal Transferase, a primer with a homopolymeric 3' end as described above, Klenow fragment, Klenow fragment exo-, DNA ligase and a DNA polymerase suitable for PCR. The kit may further comprise oligonucleotides capable to form or initiate adaptors and/or Y-shaped adaptors as described above, optionally including DNA barcodes. The kit may optionally comprise DNA cleanup equipment and reagents.

The figures show:

FIG. 1: AflI recognition sites on *Arabidopsis thaliana* Chromosome I

The chromosome position of each predicted recognition site is plotted against its index, that is its number. The curve indicates a uniform distribution of about 3100 AflI recognition sites along chromosome I, thus enabling for a representative sequence analysis. The graph obtained is similar for the other chromosomes and for different species.

Figure 2A:
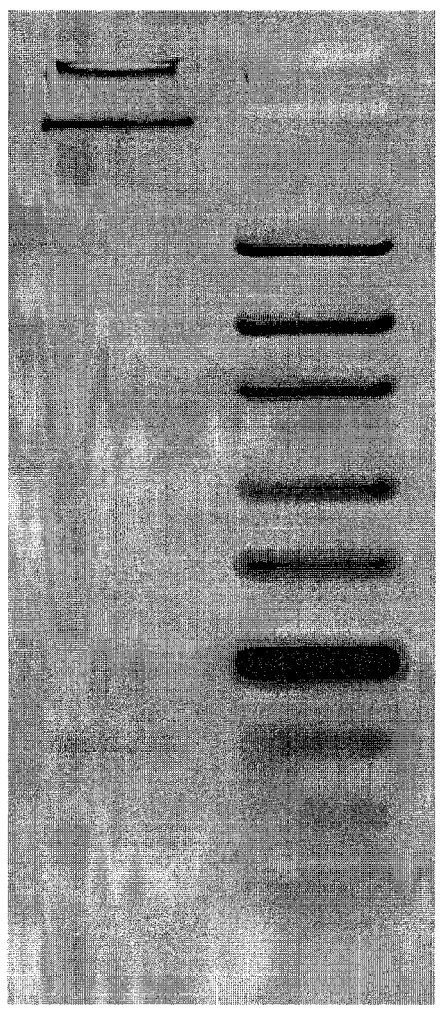
Figure 2B:
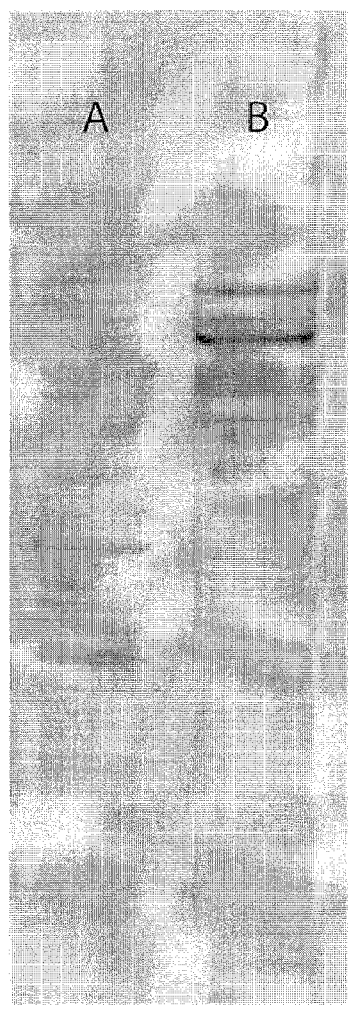

FIG. 2: Result of digest of lambda DNA with BcgI

A Lambda DNA was digested with BcgI (New England Biolabs) according to the manufacturer's instructions and the fragments obtained were subsequently separated on a 5% agarose gel. Left lane: separation of Lambda DNA digest; right lane: marker (Fermentas Ultra Low Range). The distinct band on the gel corresponds to the fraction containing the double-stranded DNA fragments comprising the BcgI recognition site (36 base pairs per strand including two-basepair overhangs at each 3'-end).

B Depicted is a 2.5% agarose gel separating A) 50-bp ladder size marker (Fermentas) and B) DNA from a BcgI restriction digest of 1 µg Lambda DNA (Fermentas). The grey shadow in lane B just below the lowest band in lane A (50-bp size) are the 36-bp fragments to be sequenced.

FIG. 3: Scheme for the production of DNA fragments with different adaptors on each end.

The sequences in FIG. 3 correspond to SEQ ID NOs 3 to 10 in the order Depicted in FIG. 3.

Step 1: Digesting sample(s) with a Type JIB restrictions enzyme and isolating the ~36-bp fraction. Step 2: Synthesizing a homopolymeric polynucleotide tail onto each of the 3'-ends of the restriction fragments using Terminal Transferase (e.g. New England Biolabs), randomly terminated by a ddNTP. Step 3: Annealing a single-stranded oligonucleotide/primer comprising a homopolymeric 3'-end complementary to the homopolymeric polynucleotide tail attached to the restriction fragments. The polynucleotide 3'-end of the primer terminates with a nucleotide different from the nucleotide used in the homopolymeric stretch of the primer in order to favour annealing of the primer to the beginning of the homopolymeric polynucleotide tail attached to the restriction fragments. Step 4: By adding Klenow fragment and dNTPs, unpaired nucleotides will be removed by the 3'-5' exonuclease activity of the Klenow fragment and the respective complementary strands of the partially annealed DNA molecules are synthesized by the polymerase activity of the Klenow fragment. The number of DNA molecules theoretically doubles in the process, because both strands will acquire a complementary strand. Step 5: "A-tailing" of the double stranded DNA fragments obtained in step 4, by adding Klenow (exo-) and dATPs. Step 6: Ligating an adaptor having a 5'-overhanging T (T-tail) to the A-tailed DNA molecule with DNA Ligase. (If the oligonucleotide used in step 3 was not blocked at the 5' end, then this would ligate to both ends.) Step 7: Amplification of the ligation products, thereby attaching desired terminal sequences.

FIG. 4: Sequencing of BcgI fragments of BcgI-digested lambda DNA

The sequences in FIG. 4 correspond to the sequences of SEQ ID NOs 11 to 18 in the order depicted in FIG. 4. FIG. 4 shows a screenshot of sequence analysis of sequenced barcoded tags stemming from processing DNA from the Phage Lambda through the procedure of the present invention using the Type JIB enzyme BcgI (New England Biolabs).

Figure 5:
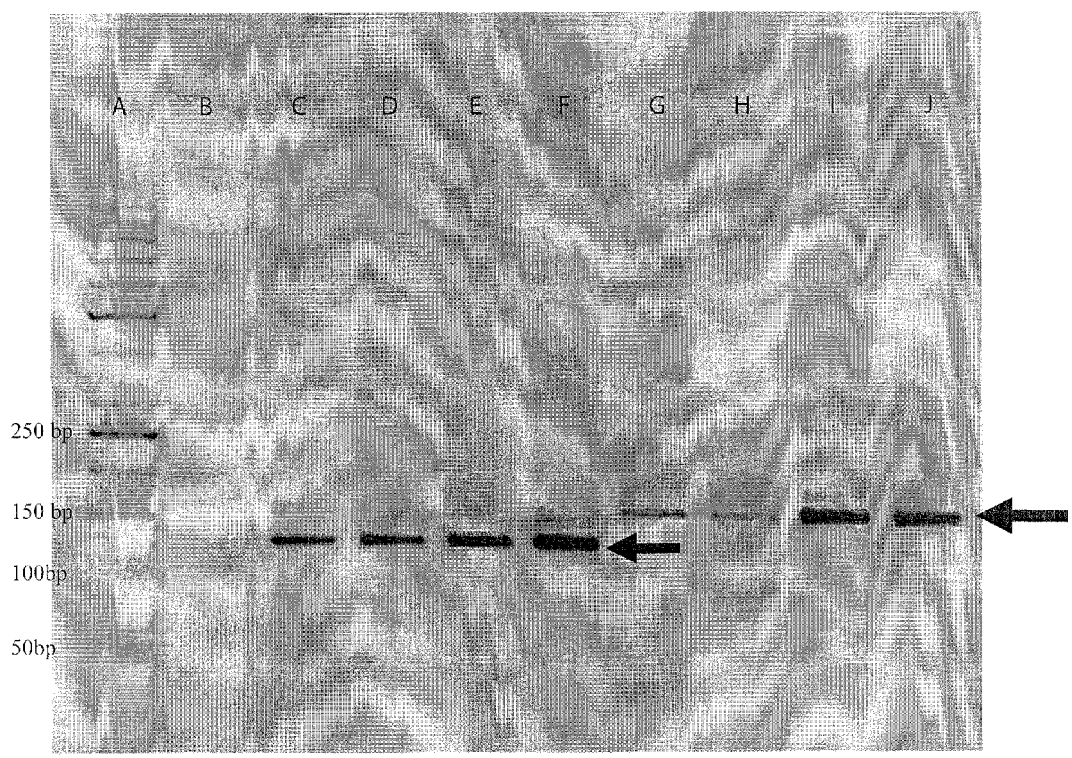

FIG. 5: Comparison of a Y-shaped DNA adaptor attached to DNA fragments in different concentrations Depicted is a 2.5% agarose gel separating the products after the enrichment/barcoding PCR.

Lane A: 50 bp-ladder size marker (Fermentas)

Lanes B-F: resulting DNA after enrichment PCRs (without barcoding oligo) where different adaptor concentrations had been used for the ligation. The size of the dominant product (red arrow) is approximately 125 bp, which is the expected size (compare to FIG. 6), and the reaction is stable across a broad range of adaptor concentrations.

Lanes G-J: enrichment PCR included barcoding oligos. The expected sizes are approximately 150 bp, which is the expected size. (compare to FIG. 6)

In all ligations adaptors formed with LNA oligos had been used. Note the complete absence of adaptor-adaptor ligation products.

Figure 6:
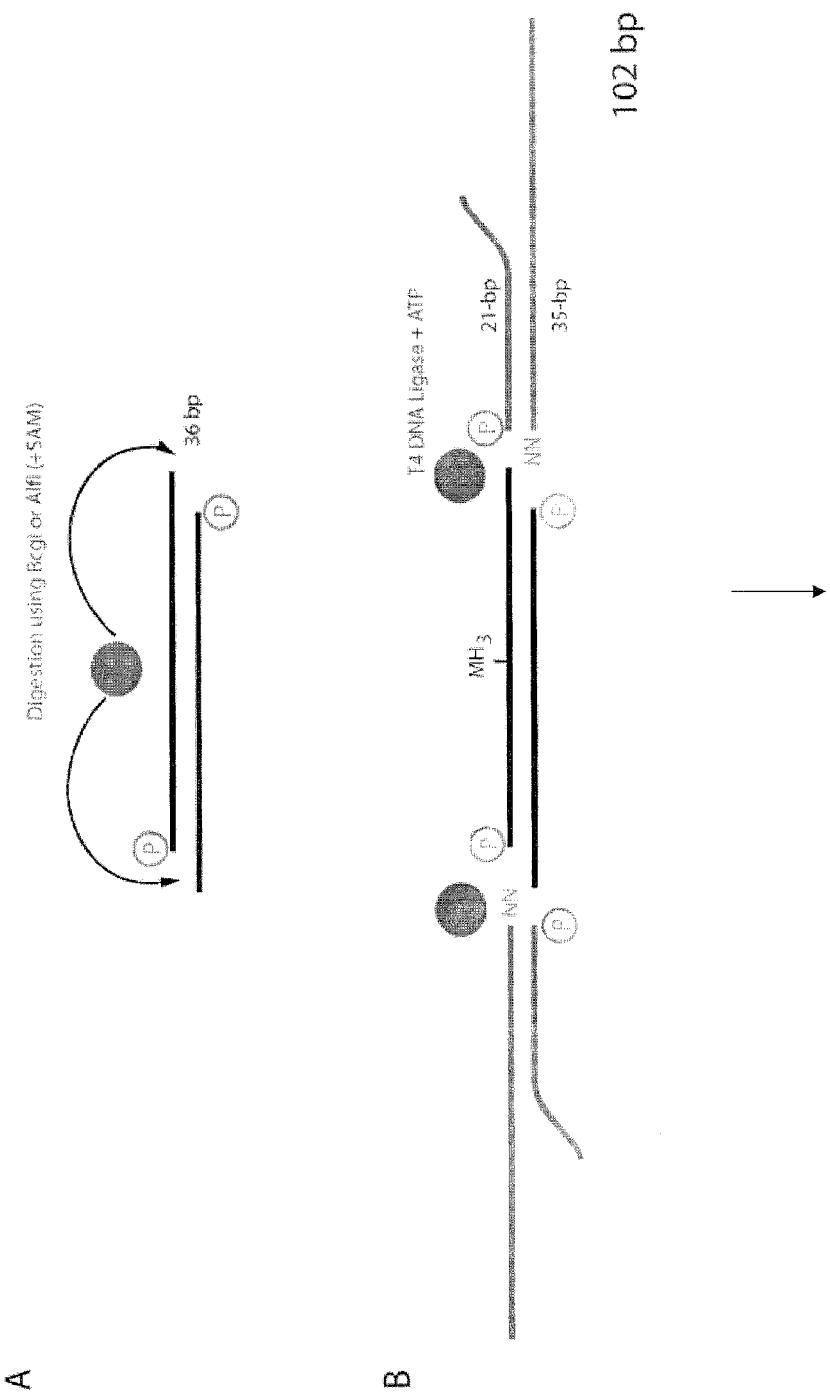
Figure 6:
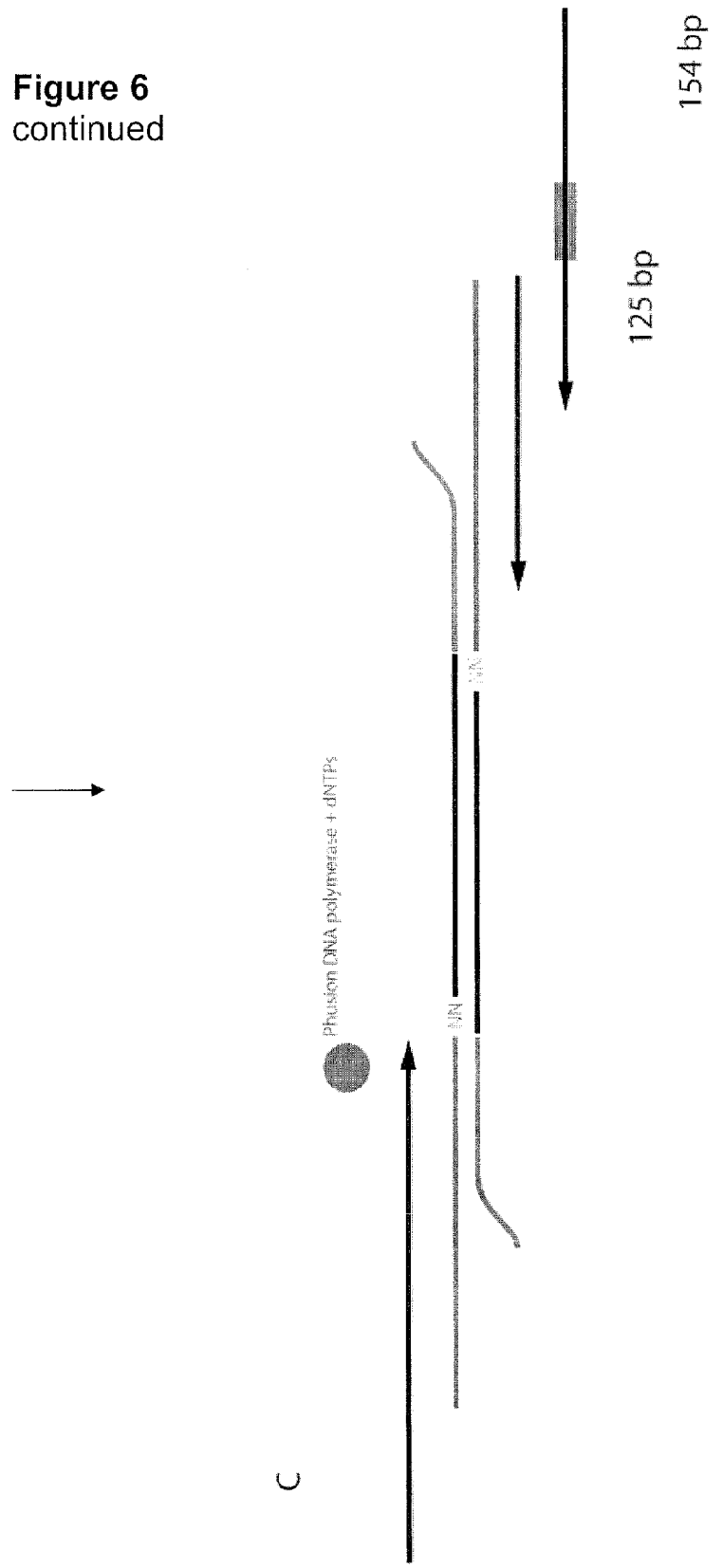

FIG. 6: Scheme for the production of DNA fragments with Y-shaped adaptor DNA at the ends.

A: Digestion of DNA Molecules (or Pools Thereof) with a Type IIB Restriction Endonuclease, e.g., BcgI.

The double stranded 36-bp short DNA fragments resulting from digestion with BcgI have 2-bp long overhangs on both 3' ends, the 5' ends are phosphorylated and the fragments are methylated at the enzyme's recognition sequences. This methylase activity is a general intrinsic property of Type MB enzymes. The methylation reaction happens simultaneously to the restriction reaction and the methylgroup then prevents subsequent digestion of this molecule using this recognition site.

B: Ligation of "Y-Shaped" Double Stranded DNA Adaptors to the Restriction Fragments.

The adaptors are produced by annealing 2 single stranded DNA oligonucleotides. They are designed such that upon pairing a 2-bp long overhang of all possible sequences ("NN") at one 3' end is juxtaposed to a phosphorylated 5'-end creating a "sticky end" for efficient ligation. At the opposite side of the adaptor the sequences do not pair (Y-shaped). Hence, after ligation of both DNA strands on both sides, using T4 DNA ligase, a ligation product is generated where both ends of each DNA (single) strand differ, which is a prerequisite for current $2^{nd}$ generation sequencing technologies. Possible presence of remaining and active Type IIB endonuclease from the previous restriction reaction does not interfere with the ligation, because the fragments are no longer a substrate for the endonuclease, because they are methylated.

C: PCR for Enrichment and/or Barcoding.

The appropriate and desired DNA fragments can now be amplified by PCR. Different ends suitable and required by the $2^{nd}$ generation sequencing technology used (and optionally barcodes) can be added in the process, simply by modifying the PCR primers.

The example illustrates the invention.

EXAMPLE 1

A sequence analysis of sequenced barcoded tags stemming from processing DNA from the Phage Lambda has been performed using the procedure of the present invention depicted in FIG. 3. The class IIB enzyme used was BcgI (New England Biolabs). The DNA was treated as described and the barcode "AACCA" (shaded in medium grey) was attached. Resulting 130 bp fragments were cloned and sequenced (the additional "T" following the barcode and also shaded in medium grey is the overhang needed for efficient ligation, "NT-tail"). The results of the experiment are depicted in FIG. 4.

The bottom of FIG. 4 designated "Reading Lambda" represents the Lambda genome as horizontal black line, above which the BcgI restriction sites are indicated as short vertical black lines. There are 28 such sites in the genome of Phage Lambda.

The bottom of the middle part of FIG. 4 ("Template Display Lambda") shows the genome (48,000 bp) represented as horizontal white line, with the restriction sites highlighted as horizontal bars. Light and dark bars are equivalent and mean that reads representing this recognition site have been sequenced, whereas sites indicated in white where not represented.

Stacked on top of the white line above are the individual reads. An arrow for each read is pointing into the direction of sequencing and hence provides indication as to which strand was sequenced.

A close-up view of the stack of reads on top of the BcgI restriction site at around 30,220 bp in the Lambda genome (indicated by a vertical line in the middle and bottom picture) is shown at the top right corner of FIG. 4. The site is represented by 6 reads, 4 forward and 2 reverse reads. Forward reads end in poly-T and reverse reads start with poly-A; the polynucleotide stretches are highlighted in dark grey, the recognition sequences of BcgI in light grey and the 5-bp barcode plus the A/T base attached for efficient ligation is highlighted in medium grey.

EXAMPLE 2

Attachment of Y-shaped adaptors to DNA fragments obtained after digestion with the class IIB restriction endonuclease BcgI.

The procedure achieves the production of barcoded Type IIB restriction enzyme fragments—ready for $2^{nd}$ generation sequencing—in 3 steps, which can be performed consecutively within the same reaction tube without intermediate cleanup. The procedure is depicted in FIG. 6. The restriction endonuclease used is the Type IIB enzyme BcgI, which yields 36-bp fragments with 2-bp long 3' overhangs of unknown sequence. The procedure will generally work for Type IIB enzymes with only minor modifications to the adaptors, which are necessary to accommodate the different single strand overhangs created upon digestion (see also e.g. Marshall and Halford, 2007).

Protocol on the example of digestion of genomic DNA of phage Lambda with BcgI:

BcgI Digests:
2 Units of enzyme in 20 µl digestion reaction:
combine 3.3 µl Lambda genomic DNA (=1 µg DNA, Fermentas)+13.7 µl H2O, 2 µl buffer SAM mix (NEB buffer 3 plus SAM as recommended by NEB), 1 µl BcgI (NEB, 2 U)
incubate>2.5 h at 37° C. (possibly over night)
Preparation of Adaptors:
DNA sequences of oligonucleotides to form adaptor:

```
                                              (SEQ ID NO: 1)
5'-Phos-AGATCGGAAGAGCACACGTCT-3'

(SEQ ID NO: 2)
5'-ACACTCTTTCCCTACACGACGCTCTTCCGATCTNN-3'
```

Sequences of perfect complementarity, which facilitate the pairing to form the double stranded DNA adaptor, are underlined. At the 3'-end, a degenerate two base overhang is present, whereas at the 5'-end, a 5'-phosphate group is attached. This is a modified Solexa© adaptor (2006 Illumina, Inc., all rights reserved). A possible variation is to use oligonucleotides with LNA© (Locked-nucleic-acid, Exiqon) bases. If placed in the region of perfect complementarity, they greatly increase the binding energy and hence make the adaptor double strand more stable.

Combine complementary adaptor oligos at 10 µM in 1×AB buffer (10×AB: 500 mM NaCl, 100 mM Tris-Cl, pH 7.5-8.0).
heat to 95° C. and let cool to room temperature
dilute adaptor to 200 nM concentration in 1×AB buffer
Ligation Reaction:
From the 20 µl digestion reaction take 10 µl and add 2 µl Ligase buffer (10×), 2 µl PEG 6000, 2 µl ATP (10 mM), 2 µl Adaptor (200 nM), 1 µl T4-DNA Ligase (10 U)
Incubate>3 h at 16° C. (possibly over night)
Enrichment and Barcoding PCR
To 4 µl of the ligation reaction add, 3.5 H20, 3 µl buffer (Phusion, 10×), 1.5 µl dNTPs (2 µM), 3 µl primermix* (10 µM), 0.15 µl Phusion DNA Polymerase.
Perform a PCR in a thermocycler to amplify the desired short fragments (~150 bp), e.g., by 18 cycles of 93° C. (10 s), 62° C. (20 s), 72° C. 10 s) using suitable PCR primers.
Purify the resulting and desired DNA fragments e.g., by Agarose gel electrophoresis; and sequence on a $2^{nd}$ generation sequencing platform such as the Illumina genome analyzer.

*The primermix is an equimolar mix of forward and reverse primer, possibly containing an additional primer with a barcode sequence, if so then the concentration of the reverse primer is to be reduced. The barcode may also be incorporated into the reverse primer.

---

The invention claimed is:

1. A method for genotyping DNA molecules contained in at least one DNA sample, the DNA molecules comprising a recognition site for a class IIB restriction endonuclease, the method comprising:
  (i) digesting the DNA molecules contained in at least one DNA sample with a class IIB restriction endonuclease to generate DNA fragments, each of the DNA fragments having a 3' end and a 5' end;
  (ii) optionally separating DNA fragments comprising the recognition site for said class IIB restriction endonuclease from the DNA fragments without the recognition site for the class IIB restriction endonuclease;
  (iii) attaching at least one adaptor DNA to the 5' end or the 3' end, or both the 5' and the 3' ends, of one or both strands of the DNA fragments comprising the recognition site for said class IIB restriction endonuclease obtained in (i) or separated in (ii) to form adaptor-fragment constructs,
  wherein said attaching of the adaptor DNA is carried out using the method of attaching different DNA adaptors to the 3' and the 5' end of a DNA molecule comprising:
  a) attaching a poly-dNTP strand terminated by ddNTP to each 3' end of a single- or double-stranded DNA molecule, wherein all dNTPs are the same and wherein N in ddNTP is not N in dNTP;
  b) annealing a primer comprising a 3' poly-dNTP strand complementary to the poly-dNTP strand attached in a), wherein the N in the 3' terminal dNTP is different from the N of the remaining poly-dNTP strand, to the nucleic acid strand of b), wherein the 5' end of said primer is blocked;
  c) removing the unpaired nucleotides of the poly-dNTP strand produced in a) and filling-in the 3' ends of both DNA strands to form blunt ended double stranded DNA fragments;
  d) adding a dNMP to the 3' end of each DNA strand;
  e) ligating to each double strand having a 3' dNMP overhang and a 5' phosphate a double stranded DNA adaptor having a 3' dNMP overhang complementary to the 3' overhang of said double strand; and, optionally,
  f) amplifying the DNA obtained in e);
  (iv) determining a nucleic acid sequence data of at least a fraction of the DNA fragments obtained in (iii); and
  (v) assigning genotypes to said at least one DNA sample analysed based on the sequence data obtained in (iv).

2. The method of claim 1, wherein said at least one DNA sample is a plurality of DNA samples and wherein said adaptor DNA attached in (iii):
  (1) comprises a DNA barcode specific for each DNA sample; or
  (2) is amplified using at least one primer binding to said adaptor DNA, wherein said primer comprises a DNA barcode specific for each DNA sample; and
  wherein step (iv) further comprises determining a nucleic acid sequence of the DNA barcode specific for each sample.

3. The method of claim 1, wherein step (v) comprises comparing the nucleic acid sequence data of said at least one DNA sample with those of a reference DNA sample and analysing for differences in the nucleic acid sequence of at least one DNA fragment of said at least one DNA sample analysed as compared to said reference DNA.

4. The method of claim 2, wherein step (v) comprises comparing the nucleic acid sequence data of the DNA samples forming said plurality of DNA samples with each other and analysing for differences in the nucleic acid sequence of at least one DNA fragment of at least one DNA sample analysed.

5. The method of claim 1 further comprising, after step (iii) and prior to step (iv) amplifying said adaptor-fragment constructs.

6. The method of claim 1, further comprising immobilising the adaptor-fragment constructs obtained in (iii) on a solid surface prior to (iv).

7. The method of claim 6, wherein there are more than one DNA samples and wherein said adaptor-fragment constructs of all DNA samples are pooled prior to immobilization.

8. The method of claim 1, wherein said determining of the sequence is effected starting from both ends of the adaptor-fragment constructs.

9. The method of claim 1, wherein said attaching of the adaptor DNA is carried out using a Y-shaped adaptor DNA.

* * * * *